US010555775B2

(12) United States Patent
Hoffman et al.

(10) Patent No.: US 10,555,775 B2
(45) Date of Patent: Feb. 11, 2020

(54) METHODS AND SYSTEM FOR PERFORMING 3-D TOOL TRACKING BY FUSION OF SENSOR AND/OR CAMERA DERIVED DATA DURING MINIMALLY INVASIVE ROBOTIC SURGERY

(75) Inventors: Brian David Hoffman, Sunnyvale, CA (US); David Q. Larkin, Menlo Park, CA (US); Giuseppe Prisco, Mountain View, CA (US); Guanghua G Zhang, San Jose, CA (US); Rajesh Kumar, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 2719 days.

(21) Appl. No.: 11/130,471

(22) Filed: May 16, 2005

(65) Prior Publication Data
US 2006/0258938 A1 Nov. 16, 2006

(51) Int. Cl.
*A61B 5/06* (2006.01)
*A61B 1/00* (2006.01)
(Continued)

(52) U.S. Cl.
CPC .......... *A61B 34/20* (2016.02); *A61B 1/00193* (2013.01); *A61B 1/04* (2013.01);
(Continued)

(58) Field of Classification Search
CPC ......... A61B 34/20; A61B 34/30; A61B 34/37; A61B 5/06; A61B 5/061; A61B 5/062;
(Continued)

(56) References Cited

U.S. PATENT DOCUMENTS 3,740,779 A 6/1973 Rubricuis
4,312,363 A 1/1982 Rothfuss et al.
(Continued)

FOREIGN PATENT DOCUMENTS

EP 469966 A1 2/1992
EP 1125557 A2 8/2001
(Continued)

OTHER PUBLICATIONS

Niemann et al., Image-Based Modeling and Its Application in Image Processing, 2004, Pattern Recognition and Image Analysis, vol. 14, No. 2, 184-189.*
(Continued)

*Primary Examiner* — Boniface N Nganga

(57) ABSTRACT

Methods and system perform tool tracking during minimally invasive robotic surgery. Tool states are determined using triangulation techniques or a Bayesian filter from either or both non-endoscopically derived and endoscopically derived tool state information, or from either or both non-visually derived and visually derived tool state information. The non-endoscopically derived tool state information is derived from sensor data provided either by sensors associated with a mechanism for manipulating the tool, or sensors capable of detecting identifiable signals emanating or reflecting from the tool and indicative of its position, or external cameras viewing an end of the tool extending out of the body. The endoscopically derived tool state information is derived from image data provided by an endoscope inserted in the body so as to view the tool.

17 Claims, 8 Drawing Sheets

(51) Int. Cl.
  *A61B 1/04* (2006.01)
  *A61B 1/313* (2006.01)
  *A61B 34/20* (2016.01)
  *A61B 34/30* (2016.01)
  *A61B 34/37* (2016.01)
  *A61B 90/00* (2016.01)
  *A61B 5/00* (2006.01)
  *A61B 34/10* (2016.01)

(52) U.S. Cl.
  CPC .............. *A61B 1/3132* (2013.01); *A61B 5/06* (2013.01); *A61B 5/061* (2013.01); *A61B 34/30* (2016.02); *A61B 34/37* (2016.02); *A61B 90/36* (2016.02); *A61B 5/062* (2013.01); *A61B 5/725* (2013.01); *A61B 90/361* (2016.02); *A61B 90/39* (2016.02); *A61B 2034/102* (2016.02); *A61B 2034/2065* (2016.02); *A61B 2090/0818* (2016.02); *A61B 2090/364* (2016.02)

(58) Field of Classification Search
  CPC ....... A61B 5/725; A61B 90/36; A61B 90/361; A61B 90/39; A61B 1/00193; A61B 1/04; A61B 1/3132; A61B 2090/364; A61B 2090/0818; A61B 2034/102
  USPC .......... 600/423, 424; 606/130; 700/245, 262
  See application file for complete search history.

(56) References Cited

U.S. PATENT DOCUMENTS

| | | | |
|---|---|---|---|
| 4,614,366 A | 9/1986 | North et al. | |
| 4,725,965 A | 2/1988 | Keenan | |
| 4,753,569 A | 6/1988 | Pryor | |
| 4,754,415 A | 6/1988 | George et al. | |
| 4,826,391 A | 5/1989 | Lawrence et al. | |
| 4,831,549 A | 5/1989 | Red et al. | |
| 4,922,909 A | 5/1990 | Little et al. | |
| 5,047,701 A | 9/1991 | Takarada et al. | |
| 5,078,140 A | 1/1992 | Kwoh | |
| 5,086,401 A | 2/1992 | Glassman et al. | |
| 5,388,059 A | 2/1995 | Dementhon | |
| 5,402,801 A | 4/1995 | Taylor | |
| 5,487,172 A | 1/1996 | Hyatt | |
| 5,572,999 A | 11/1996 | Funda | |
| 5,579,444 A | 11/1996 | Dalziel et al. | |
| 5,603,318 A | 2/1997 | Heilbrun et al. | |
| 5,630,431 A | 5/1997 | Taylor | |
| 5,649,021 A | 7/1997 | Matey et al. | |
| 5,676,673 A * | 10/1997 | Ferre | A61B 34/20 606/130 |
| 5,797,849 A | 8/1998 | Vesely et al. | |
| 5,797,900 A | 8/1998 | Madhani et al. | |
| 5,820,545 A | 10/1998 | Arbter et al. | |
| 5,836,869 A | 11/1998 | Kudo et al. | |
| 5,950,201 A | 9/1999 | Van Huben et al. | |
| 5,950,629 A | 9/1999 | Taylor et al. | |
| 5,959,425 A | 9/1999 | Bieman et al. | |
| 6,036,637 A | 3/2000 | Kudo | |
| 6,106,511 A | 8/2000 | Jensen | |
| 6,122,541 A | 9/2000 | Cosman et al. | |
| 6,167,296 A | 12/2000 | Shahidi | |
| 6,197,296 B1 | 3/2001 | Shahidi | |
| 6,201,984 B1 | 3/2001 | Funda et al. | |
| 6,231,526 B1 | 5/2001 | Taylor et al. | |
| 6,235,038 B1 | 5/2001 | Hunter et al. | |
| 6,246,900 B1 | 6/2001 | Cosman et al. | |
| 6,278,906 B1 | 8/2001 | Piepmeier et al. | |
| 6,292,715 B1 | 9/2001 | Rongo | |
| 6,332,089 B1 | 12/2001 | Acker et al. | |
| 6,346,072 B1 | 2/2002 | Cooper | |
| 6,425,865 B1 | 7/2002 | Salcudean et al. | |
| 6,434,416 B1 | 8/2002 | Mizoguchi et al. | |
| 6,434,507 B1 | 8/2002 | Clayton et al. | |
| 6,459,926 B1 | 10/2002 | Nowlin et al. | |
| 6,468,265 B1 | 10/2002 | Evans et al. | |
| 6,470,207 B1 * | 10/2002 | Simon et al. | 600/426 |
| 6,484,049 B1 | 11/2002 | Seeley et al. | |
| 6,490,475 B1 | 12/2002 | Seeley et al. | |
| 6,493,608 B1 | 12/2002 | Niemeyer | |
| 6,498,944 B1 | 12/2002 | Ben-Haim et al. | |
| 6,522,906 B1 * | 2/2003 | Salisbury et al. | 600/407 |
| 6,529,765 B1 | 3/2003 | Franck et al. | |
| 6,533,737 B1 | 3/2003 | Brosseau et al. | |
| 6,587,750 B2 | 7/2003 | Gerbi et al. | |
| 6,591,130 B2 | 7/2003 | Shahidi | |
| 6,594,552 B1 | 7/2003 | Nowlin et al. | |
| 6,659,939 B2 | 12/2003 | Moll et al. | |
| 6,665,554 B1 | 12/2003 | Charles et al. | |
| 6,668,677 B2 | 12/2003 | Knappe et al. | |
| 6,671,581 B2 | 12/2003 | Niemeyer et al. | |
| 6,714,839 B2 | 3/2004 | Salisbury et al. | |
| 6,725,080 B2 | 4/2004 | Melkent et al. | |
| 6,741,911 B2 | 5/2004 | Simmons | |
| 6,770,081 B1 | 8/2004 | Cooper et al. | |
| 6,782,287 B2 | 8/2004 | Grzeszczuk et al. | |
| 6,785,593 B2 | 8/2004 | Wang et al. | |
| 6,799,065 B1 | 9/2004 | Niemeyer | |
| 6,799,088 B2 | 9/2004 | Wang et al. | |
| 6,804,581 B2 | 10/2004 | Wang et al. | |
| 6,816,755 B2 | 11/2004 | Habibi et al. | |
| 6,817,972 B2 | 11/2004 | Snow | |
| 6,690,963 B2 | 12/2004 | Ben-Haim et al. | |
| 6,845,190 B1 * | 1/2005 | Smithwick | A61B 1/0008 385/1 |
| 6,856,826 B2 | 2/2005 | Seeley | |
| 6,856,827 B2 | 2/2005 | Seeley | |
| 6,866,671 B2 | 3/2005 | Tierney et al. | |
| 6,871,117 B2 | 3/2005 | Wang et al. | |
| 6,951,535 B2 | 10/2005 | Ghodoussi et al. | |
| 6,978,167 B2 | 12/2005 | Dekel et al. | |
| 7,008,373 B2 | 3/2006 | Stoianovici et al. | |
| 7,074,179 B2 | 7/2006 | Wang et al. | |
| 7,155,315 B2 | 12/2006 | Niemeyer et al. | |
| 7,155,316 B2 | 12/2006 | Sutherland et al. | |
| 7,162,338 B2 | 1/2007 | Goncalves et al. | |
| 7,166,112 B2 | 1/2007 | Hawkins et al. | |
| 7,182,770 B2 | 2/2007 | Falahee | |
| 7,194,118 B1 | 3/2007 | Harris et al. | |
| 7,272,467 B2 | 9/2007 | Goncalves et al. | |
| 7,277,120 B2 | 10/2007 | Gere et al. | |
| 7,283,654 B2 | 10/2007 | McLain | |
| 7,359,746 B2 | 4/2008 | Arata | |
| 7,413,565 B2 | 8/2008 | Wang et al. | |
| 7,453,227 B2 | 11/2008 | Prisco et al. | |
| 7,457,698 B2 | 11/2008 | Danko | |
| 7,458,936 B2 | 12/2008 | Zhou et al. | |
| 7,464,596 B2 | 12/2008 | Bui et al. | |
| 7,545,965 B2 | 6/2009 | Suzuki et al. | |
| 7,571,025 B2 | 8/2009 | Bischoff | |
| 7,612,805 B2 | 11/2009 | Solomon | |
| 7,664,571 B2 | 2/2010 | Gonzalez-Banos et al. | |
| 7,689,014 B2 | 3/2010 | Abovitz et al. | |
| 7,689,321 B2 | 3/2010 | Karlsson | |
| 7,756,608 B2 | 7/2010 | Brogardh | |
| 7,962,313 B2 | 6/2011 | Chu et al. | |
| 8,073,528 B2 | 12/2011 | Zhao et al. | |
| 8,108,072 B2 | 1/2012 | Zhao et al. | |
| 8,147,503 B2 | 4/2012 | Zhao et al. | |
| 8,218,727 B2 | 7/2012 | Baumgart et al. | |
| 8,473,031 B2 | 6/2013 | Nixon et al. | |
| 8,792,963 B2 | 7/2014 | Zhao et al. | |
| 2002/0151784 A1 * | 10/2002 | Mizoguchi | G02B 21/0012 600/407 |
| 2002/0156345 A1 | 10/2002 | Eppler et al. | |
| 2003/0029464 A1 | 2/2003 | Chen et al. | |
| 2003/0055410 A1 * | 3/2003 | Evans | A61B 34/32 606/1 |
| 2003/0109780 A1 | 6/2003 | Coste-Maniere et al. | |
| 2003/0163142 A1 | 8/2003 | Paltieli et al. | |
| 2003/0208296 A1 * | 11/2003 | Brisson | A61B 90/10 700/117 |
| 2003/0210812 A1 | 11/2003 | Khamene et al. | |

(56) References Cited

U.S. PATENT DOCUMENTS

| | | | |
|---|---|---|---|
| 2004/0052333 | A1 | 3/2004 | Sayre et al. |
| 2004/0243147 | A1 | 12/2004 | Lipow |
| 2005/0054910 | A1 | 3/2005 | Tremblay et al. |
| 2005/0102063 | A1 | 5/2005 | Bierre |
| 2005/0193451 | A1 | 9/2005 | Quistgaard et al. |
| 2005/0234679 | A1 | 10/2005 | Karlsson |
| 2006/0041181 | A1 | 2/2006 | Viswanathan et al. |
| 2006/0058919 | A1 | 3/2006 | Sommer |
| 2006/0142657 | A1 | 6/2006 | Quaid et al. |
| 2006/0161045 | A1 | 7/2006 | Merril et al. |
| 2006/0241414 | A1 | 10/2006 | Nowlin et al. |
| 2007/0021738 | A1 | 1/2007 | Hasser et al. |
| 2007/0038080 | A1 | 2/2007 | Salisbury, Jr. et al. |
| 2007/0078334 | A1 | 4/2007 | Scully et al. |
| 2007/0156017 | A1 | 7/2007 | Lamprecht |
| 2007/0161854 | A1 | 7/2007 | Alamaro et al. |
| 2007/0167702 | A1 | 7/2007 | Hasser et al. |
| 2007/0183041 | A1 | 8/2007 | McCloy et al. |
| 2007/0211927 | A1 | 9/2007 | Groszmann et al. |
| 2007/0265527 | A1 | 11/2007 | Wohlgemuth |
| 2008/0004603 | A1 | 1/2008 | Larkin et al. |
| 2008/0013809 | A1 | 1/2008 | Zhu et al. |
| 2008/0033240 | A1 | 2/2008 | Hoffman et al. |
| 2008/0065109 | A1 | 3/2008 | Larkin |
| 2008/0255445 | A1 | 10/2008 | Neubauer et al. |
| 2008/0285724 | A1 | 11/2008 | Dehler |
| 2009/0036902 | A1 | 2/2009 | Dimaio et al. |
| 2009/0037278 | A1 | 2/2009 | Cohen et al. |
| 2009/0171332 | A1 | 7/2009 | Bonneau |
| 2009/0192524 | A1 | 7/2009 | Itkowitz et al. |
| 2009/0248036 | A1 | 10/2009 | Hoffman et al. |
| 2009/0268010 | A1 | 10/2009 | Zhao et al. |
| 2009/0268011 | A1 | 10/2009 | Scott et al. |
| 2009/0268012 | A1 | 10/2009 | Scott et al. |
| 2009/0268015 | A1 | 10/2009 | Scott et al. |
| 2009/0270678 | A1 | 10/2009 | Scott et al. |
| 2009/0324009 | A1 | 12/2009 | Schulz |
| 2009/0326553 | A1 | 12/2009 | Mustufa et al. |
| 2010/0164950 | A1 | 7/2010 | Zhao et al. |
| 2010/0166323 | A1 | 7/2010 | Zhao et al. |
| 2010/0168562 | A1 | 7/2010 | Zhao et al. |
| 2010/0168763 | A1 | 7/2010 | Zhao et al. |
| 2010/0245541 | A1 | 9/2010 | Zhao et al. |
| 2010/0317965 | A1 | 12/2010 | Itkowitz et al. |
| 2010/0318099 | A1 | 12/2010 | Itkowitz et al. |
| 2010/0331855 | A1 | 12/2010 | Zhao et al. |
| 2012/0020547 | A1 | 1/2012 | Zhao et al. |
| 2015/0005622 | A1 | 1/2015 | Zhao et al. |
| 2017/0079725 | A1 | 3/2017 | Hoffman et al. |
| 2017/0079726 | A1 | 3/2017 | Hoffman et al. |

FOREIGN PATENT DOCUMENTS

| | | | |
|---|---|---|---|
| WO | WO-9938449 A1 | | 8/1999 |
| WO | WO/57767 | | 10/2000 |
| WO | WO 0057767 A2 | * | 10/2000 |
| WO | WO-200057767 A3 | | 1/2001 |
| WO | WO-2004019799 A2 | | 3/2004 |
| WO | WO-2005102202 A1 | | 11/2005 |
| WO | WO-2006124388 A1 | | 11/2006 |
| WO | WO-2006131373 A2 | | 12/2006 |
| WO | WO-2009085616 A1 | | 7/2009 |

OTHER PUBLICATIONS

Ruf et al.,Visual tracking of an end-effector by adaptive kinematic prediction, Intelligent Robots and Systems, 1997. IROS '97., Proceedings of the 1997 IEEE/RSJ International Conference, vol. 2, 893-899.*

Tonko et al., Towards visually servoed manipulation of car engine parts, Robotics and Automation, 1997. Proceedings., 1997 IEEE International Conference on. vol. 4. IEEE, 1997.*

McKenna et al., Towards video understanding of laparoscopic surgery: Instrument tracking, Proc. of Image and Vision Computing, New Zealand. 2005.*

Cortesao et al., Data Fusion for Robotic Assembly Tasks Based on Human Skills IEEE Transactions on Robotics, vol. 20, No. 6, Dec. 2004.*

Kumar et al., Intelligent Multi-Sensor Fusion Techniques in Flexible Manufacturing Workcells, Proceeding of the 2004 American Control Conference Boston, Massachusetts Jun. 30-Jul. 2, 2004.*

Strelow et al., Online Motion Estimation from Image and Inertial Measurements, 2003.*

Krupa, Achieving high-precision laparoscopic manipulation through adaptive force control, Advanced Robotics, vol. 18, No. 9, pp. 905-926 (2004).*

Dewan, Vision-Based Assistance for Ophthalmic Micro-Surgery, Medical Image Computing and Computer-Assisted Intervention, vol. 3217 of the series Lecture Notes in Computer Science pp. 49-57 (2004).*

Niemann, Image-Based Modeling and Its Application in Image Processing, Pattern Recognition and Image Analysis, vol. 14, No. 2, 2004, pp. 184-189.*

Westmore, Direct Dynamic Control of a Robot Using an End-Point Mounted Camera and Kalman Filter Position Estimation, Proceedings of the 1991 EEEInternational Conference on Robotics and Autanatim Sacramento, California—Apr. 1991.*

PCT/US06/17832 International Search Report, dated Sep. 25, 2006, 4 pages.

PCT/US06/17832 Written Opinion of the International Search Authority, dated Sep. 25, 2006, 7 pages.

Zhang,:Journal of Robotix Systems, vol. 19, No. 7 PP315-328, 2002.

Plaenkers: Proceedings of the 7th European Conference on Computer Vision—Part II pp. 325-339, May 28-31, 2002.

Senior: IEE Workshop on Visual Surveillance/Pets, Nice, France, Oct. 2003.

Drummond: International Conference of Computer Vision(ICCV'01), vol. 2, pp. 315-320, Jul. 7-14, Vancouver, Canada.

Marchand; IEEE Internationl Conference on Computer Vision (ICCV'99), vol. 1, pp. 262-268, Sep. 1999, Kerkira, Greece.

Welch: An Introduction to the Kalman Filter, UNC—Chapel Hill, TR95-041, Apr. 5, 2004.

Wei,:IEE Engineering in Medicine and Biology, 0739-5175; Jan./Feb. 1997.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

Drummond, et al., "Real-time tracking of highly articulated structures in the presence of noisy measurements," Proc. International Conference on Computer Vision, Vancouver, Canada, 2001, pp. 315-320.

Marchand, et al., "Robust real-time visual tracking using a 2D-3D model-based approach." Seventh Annual IEEE International Conference on Computer Vision (ICCV), Sep. 20-27, 1999, vol. 1, pp. 262-268.

Plaenkers and Fua, "Model-based silhouette extraction for accurate people tracking," Proceedings of the 7th European Conference on Computer Vision—Part II, pp. 325-339. vol. 2351, Springer-Verlag, 2002.

Senior, A.W., "Real-time articulated human body tracking using silhouette information," Proceedings IEEE Workshop on Visual Surveillance/PETS, Nice, France. Oct. 2003. http://www.andrewsenior.com/papers/.

Wei, et al., "Real-time visual servoing for laparoscopic surgery: Controlling robot motion with color image segmentation," Engineering in Medicine and Biology Magazine, IEEE, vol. 16, Issue 1, Jan.-Feb. 1997, pp. 40-45.

Welch and Bishop, "An Introduction to the Kalman Filter," SIGGRAPH 2001, Updated Apr. 5, 2004.

Zhang, et al., "Application of Visual Tracking for Robot-Assisted Laparoscopic Surgery," J Robot Sys 2002, pp. 315-328, vol. 19.

(56) References Cited

OTHER PUBLICATIONS

Lee, M.F. Ricky et al., "Implementation of Sensor Selection and Fusion Using Fuzzy Logic," Joint 9th IFSA World Congress and 20th NAFIPS International Conference, Jul. 25-28, 2001, Vancouver, BC. Canada, vol. 1, pp. 328-333.
Luo, Ren C. and Min-Hsiun Lin, "Robot Multi-Sensor Fusion and Integration: Optimum Estimation of Fused Sensor Data," Proceedings of 1998 IEEE International Conference on Robotics and Automation, Apr. 24-29, 1998, Philadelphia, PA, vol. 2, pp. 1076-1081.
Nakamura, Yoshihiko and Yingti Xu, "Geometrical Fusion Method for Multi-Sensor Robotic Systems," Proceedings of the 1989 IEEE International Conference on Robotics and Automation, May 14-19, 1989, Scottsdale, AZ, vol. 2, pp. 668-673.
Oh, Paul Y. and Peter K. Allen, "Visual Servoing by Partitioning Degrees of Freedom," IEEE Transactions on Robotics and Automation, Feb. 2001, vol. 17, No. 1, pp. 1-17.
Loy, Gareth et al., "An Adaptive Fusion Architecture for Target Tracking," Proceedings of the 5th IEEE International Conference on Automatic Face and Gesture Recognition (FGR'02), May 20-21, 2002, Washington, D.C., 6 pages.
Casals, A. et al. "Automatic Guidance of an Assistant Robot in Laparoscopic Surgery," 1996 IEEE International Conference on Robotics and Automation (ICRA '96), Minneaplis, MN, Apr. 1996, pp. 895-900.
Corke, Peter I., "Visual Control of Robot Manipulators—A Review," Visual Servoing: Real-Time Control of Robot Manipulators Based on Visual Sensory Feedback, vol. 7 of Series in Robotics and Automated Systems, Ed. Koichi Hashimoto, World Scientific Publishing Ltd., London, 1993, pp. 1-31.
Delamarre, Quentin and Olivier Faugeras, "3D Articulated Models and Multi-Tracking with Sihouettes," 7th IEEE International Conference on Computer Vision, Sep. 20-27, 1999, vol. 2, pp. 716-721.
Drummond, Tom and Roberto Cipolla, "Real-Time Visual Tracking of Complex Structures," IEEE Transaction on Pattern Analysis and Machine Intelligence (PAMI), Jul. 2002, vol. 24, No. 7, pp. 932-946.
Green, Philip S. et al., "Telepresence Surgery," IEEE Engineering in Medicine and Biology Magazine, May/Jun. 1995, pp. 324-329, vol. 14—Issue 3, IEEE.
Grimson, W.E.L., et al., "An automatic registration method for frameless sterotaxy, image guided surgery, and enhanced reality visualization," IEEE Transactions on Medical Imaging, vol. 15, No. 2, Apr. 1996, pp. 129-140.
Guthart, Gary S. et al., "The IntuitiveT telesurgery system: overview and application," Proceedings of the 2000 IEEE International Conference on Robotics & Automation, 2000, pp. 618-621, vol. 1, IEEE.
Horn, Berthold K.P., "Closed-form solution of absolute orientation using unit quaternions," Journal of the Optical Society of America A, vol. 4, No. 4, pp. 629-642, Apr. 1987.
Julier, Simon J. and Jeffrey K. Uhlmann, "A New Extension of the Kalman Filter to Nonlinear Systems," The Proceedings of AeroSense: The 11th International Symposium on Aerospace/Defense Sensing, Simulation and Controls, Orlando, FL, USA, 1997. SPIE. Multi Sensor Fusion, Tracking and Resource Management II, vol. 3068, pp. 182-193.
Jung, Soon Ki and Kwang Yun Wohn, "A model-based 3-D tracking of rigid objects from a sequence of multiple perspective views," Pattern Recognition Letters, 1998, vol. 19, pp. 499-512.
Kalman R.E., "A New Approach to Linear Filtering and Prediction Problems", 1960, vol. 82, Series D, pp. 35-45.
Liu, Jun S. and Rong Chen, "Sequential Monte Carlo Methods for Dynamic Systems," Journal of the American Statistical Association, 1998, vol. 93, pp. 1032-1044.
Lowe, David G., "Fitting Parameterized Three-Dimensional Models to Images," IEEE Transactions on Pattern Analysis and Machine Intelligence Intelligence (PAMI), May 1991, vol. 13, Issue 5, pp. 441-450.
Lowe, David G., "Object Recognition from Local Scale-Invariant Features," 7th IEEE International Conference on Computer Vision, Sep. 20-27, 1999, vol. 2, pp. 1150-1157.
Martin, Frederick and Radu Horaud, "Multiple-Camera Tracking of Rigid Objects," International Journal of Robotics Research, Feb. 2002, vol. 21, No. 2, pp. 97-113.
Nitzan, David, "Three-Dimensional Vision Structure for Robot Applications," IEEE Transactions on Pattern Analysis and Machine Intelligence (PAMI), May 1998, vol. 10, No. 3, pp. 291-309.
Papanikolopoulos, N. et al. "Vision and Control Techniques for Robotic Visual Tracking," 1991 IEEE International Conference on Robotics and Automation, Apr. 9-11, 1991, vol. 1, pp. 857-864.
Papanikolopoulos, N. et al., "Visual Tracking of a Moving Target by a Camera Mounted on a Robot: A Combination of Control and Vision," IEEE Transactions on Robotics and Automation, Feb. 1993, vol. 9, No. 1, pp. 14-35.
Pope, Arthur R. and David G. Lowe, "Learning Appearance Models for Object Recognition," International Workshop on Object Representation in Computer Vision II, 1996, Lecture Notes in Computer Science, vol. 1144, pp. 201-219.
Ramussen, Christopher et al., "Probabilistic data association methods for tracking complex visual objects," IEEE Transactions on Pattern Analysis and Machine Intelligence, 2001, pp. 560-576, vol. 23, Issue 6, IEEE.
Rehg, James M. and Takeo Kanade, "Model-Based Tracking of Self-Occluding Articulated Objects," 5th International Conference on Computer Vision, Jun. 20-23, 1995. pp. 612-617.
Taylor, Russell H. et al., "A Telerobotic Assistant for Laparoscopic Surgery," IEEE Engineering in Medicine and Biology, May/Jun., 1995, pp. 279-288, vol. 14, Issue 3, IEEE.
Triggs, Bill et al., "Bundle Adjustment A Modern Synthesis," 1999, 71 Pages, Internet http://lear.inrialpes.fr/people/triggs/pubs/Triggs-va99.pdf
Uecker, Darrin R. et al, "Automated Instrument Tracking in Robotically-Assisted Laparoscopic Surgery," Journal of Image Guided Surgery, vol. 1, No. 6, pp. 308-325, 1998.
West, Jay B. and Calvin R. Maurer, Jr., "Designing Optically Tracked Instruments for Image-Guided Surgery," IEEE Transaction on Medical Imaging, vol. 23, No. 5, May 2004, pp. 533-545.
Zhao, Wenyi et al., "Face Recognition: A Literature Survey," ACM Computing Surveys, Dec. 2003, vol. 35, No. 4, pp. 399-459.
Extented European Search Report for Application No. EP13187622, dated May 22, 2014, 5 pages.
European Search Report for Application No. EP13187613, dated Dec. 20, 2013, 5 pages.
European Search Report for Application No. EP13187615, dated Dec. 20, 2013, 5 pages.
European Search Report for Application No. EP13187616, dated Dec. 20, 2013, 6 pages.
European Search Report for Application No. EP13187617, dated Dec. 20, 2013, 6 pages.
European Search Report for Application No. EP13187618, dated Jan. 8, 2014, 5 pages.
European Search Report for Application No. EP13187620, dated Dec. 20, 2013, 5 pages.
Co-pending U.S. Appl. No. 61/203,975, filed Dec. 31, 2008.
Co-pending U.S. Appl. No. 61/204,082, filed Dec. 31, 2008.
Doignon, C. et al., "Model-based 3-D pose estimation and feature tracking for robot assisted surgery with medical imaging," published in "From Features to Actions: Unifying Perspectives in Computational and Robot Vision" workshop at the IEEE International Conference on Robotics and Automation, Apr. 2007, 10 pages. Internet: http://hal.archives-ouvertes.fr/docs/00/35/06/47/PDF/2007_wkicra_doignon.pdf.
Fischler, Martin A. and Robert C. Bolles, "Random sample consensus: a paradigm for model fitting with applications to image analysis and automated cartography," Communications of the ACM, vol. 24 , No. 6, Jun. 1981, pp. 381-395.
Kim, Miriam et al., "Computer Assisted 3D Measurements for Micro-Surgery," Proceedings of the Human Factors and Ergonomics Society 41st Annual Meeting, 1997, pp. 787-791, Human Factors and Ergonomics Society.

(56) References Cited

OTHER PUBLICATIONS

Kosaka, Akio et al., "Augmented Reality System for Surgical Navigation Using Robust Target Vision," IEEE Conference on Computer Vision and Pattern Recognition, 2000, vol. 2, pp. 187-194.
Lowe, David G., "Distinctive Image Features from Scale-Invariant Keypoints," International Journal of Computer Vision, vol. 60, No. 2, Nov. 2004, pp. 91-110.
PCT/US08/77611 International Search Report and Written Opinion of the International Searching Authority, dated Jun. 12, 2009, 14 pages.
PCT/US08/77611 Invitation to Pay Additional Fees with Results of the Partial International Search, dated Feb. 24, 2009, 5 pages.
PCT/US08/86249 International Search Report, dated Mar. 27, 2009, 4 pages.
PCT/US08/86249 Written Opinion of the International Searching Authority, dated Mar. 27, 2009, 7 pages.
Taylor, Russell H., et al., "An overview of computer-integrated surgery at the IBM Thomas J. Watson Research Center," IBM J Research and Development, 1996, pp. 163-183, vol. 40, Issue 2, IBM Corp.
U.S. Appl. No. 11/865,016 Office Action, dated Dec. 23, 2010, 30 pages.
Zhao, Wenyi et al., "Alignment of Continuous Video onto 3D Point Clouds," IEEE Transactions on Pattern Analysis and Machine Intelligence (PAMI), Aug. 2005, vol. 27, No. 8, pp. 1305-1318.
Zhao, Wenyi, Table 1.1: "Comparison of related object and instrument tool tracking," from White Paper titled "Instrument Tool Tracking through Adaptive Fusion of Vision and Kinematics," Oct. 2006, p. 7.
Office Action dated May 13, 2016 for European Application No. 13187613.8 filed May8, 2006, 4 pages.
Office Action dated May 13, 2016 for European Application No. 13187815.3 filed May 8, 2006, 4 pages.
Office Action dated May 18, 2016 for European Application No. 13187617.9 filed May 8, 2006, 3 pages.
Office Action dated May 18, 2016 for European Application No. 13187620.3 filed May 8, 2006, 3 pages.
Office Action dated May 18, 2016 for European Application No. 13187622.9 filed May 8, 2006, 4 pages.
Cortesao R., et al., "Data Fusion for Compliant Motion Tasks Based on Human Skills," Intelligent Robots and Systems, 2002, IEEE/RSJ International Conference on, vol. 2, IEEE, 2002, pp. 1529-1534.
Office Action dated Mar. 5, 2018 for European Application No. 13187620.3 filed May 8, 2006, 4 pages.

\* cited by examiner

METHODS AND SYSTEM FOR PERFORMING 3-D TOOL TRACKING BY FUSION OF SENSOR AND/OR CAMERA DERIVED DATA DURING MINIMALLY INVASIVE ROBOTIC SURGERY

STATEMENT AS TO RIGHTS TO INVENTIONS MADE UNDER FEDERALLY SPONSORED RESEARCH OR DEVELOPMENT

This invention was made with United States Government Support under cooperative agreement number: 70NANB1H3048 awarded by the National Institute of Standards and Technology (NIST). The United States government has certain rights in the invention.

FIELD OF THE INVENTION

The present invention generally relates to minimally invasive surgery and in particular, to methods and a system for performing 3-D tool tracking by fusion of sensor and/or camera derived data (e.g. tool position, velocity) during minimally invasive robotic surgery.

BACKGROUND OF THE INVENTION

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for a standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch or less) incisions to provide entry ports for laparoscopic surgical instruments.

The laparoscopic surgical instruments generally include a laparoscope or an endoscope (for viewing the surgical field), and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, image capture lenses, and needle holders, for example.

To perform surgical procedures, the surgeon passes these working tools or instruments through the cannula sleeves to an internal surgical site and manipulates them from outside the abdomen. The surgeon views the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. Each of the master input devices controls the motion of a servomechanically operated surgical instrument. During the surgical procedure, the telesurgical system can provide mechanical actuation and control of a variety of surgical instruments or tools having end effectors that perform various functions for the surgeon, e.g., holding or driving a needle, grasping a blood vessel, or dissecting tissue, or the like, in response to manipulation of the master input devices.

During the surgical procedure, however, the surgeon may manipulate the tool so that its end effector is moved outside of the endoscope's field of view, or the end effector may become difficult to see due to occlusion by fluids or other intervening objects. In such cases it would be useful to be able to provide assistance to the surgeon in locating and/or identifying the end effector on the workstation's display screen.

Various techniques have been developed for identifying the tool in a camera image. One such technique is described, for example, in Guo-Qing Wei, Klaus Arbter, and Gerd Hirzinger, "Real-Time Visual Servoing for Laparoscopic Surgery," *IEEE Engineering in Medicine and Biology*, Vol. 16, No. 1, pp. 40-45, 1997, wherein a color marker is used to identify a tool in a camera image so that the camera may be automatically maneuvered so as to keep the tool in the center of its visual image. Another such mechanism is described, for example, in Xiaoli Zhang and Shahram Payandeh, "Application of Visual Tracking for Robot-Assisted Laparoscopic Surgery," *Journal of Robotics Systems*, Vol. 19, No. 7, pp. 315-328, 2002, wherein a striped marker is used to identify a tool and its depth in a camera image so that the camera may be automatically maneuvered to visually track the tool.

These techniques, however, are not generally useful when the end effector is outside the endoscope's field of view, or when it is occluded by fluid or some object. In either case, such markers cannot be found and tool identification is not possible. Second, simple color markers and other orientation independent markers placed on the tool do not facilitate determining the orientation or pose of the tool. Third, computational complexity in identifying and tracking the tool markers may make real-time tracking difficult. In particular, increased time spent processing each captured frame of video will reduce the frequency at which video capture can occur, possibly resulting in abrupt transitions from one image to the next. Fourth, uncorrected camera calibration and/or other system measurement errors may result in errors when determining tool positions and orientations from the camera's visual images.

OBJECTS AND SUMMARY OF THE INVENTION

To make each of multiple tools easily distinguishable to the surgeon on the workstation display screen and also to patient-side staff, a number of computer assisted techniques may be employed such as: predicting the position and orientation of the tool, and overlaying a computer aided design ("CAD") model of the tool, or other virtual mark or indicator, over the predicted position and orientation of the tool in the display screen; predicting the position and orientation of the tool, and uniquely marking each tool at its predicted position and orientation to make it distinguishable from other tools on the display screen; and predicting the position and orientation of the tool, and erasing or brushing out the shaft of the tool while highlighting its end effector in some fashion so that the end effector seemingly floats in and stands out on the display screen.

One advantage, for example, of uniquely marking each tool at its predicted position and orientation to make it distinguishable from other tools on the display screen, is that it a) makes it easier for the surgeon (who only sees the tools inside the body) to communicate with a patient-side staff (who only see the tools outside the body) about specific tools, and b) makes sure the surgeon is aware of tools that might be outside the field of view. This is especially important when there are more than two tools, since the surgeon may see only two and assume those are the two he is controlling with his two hands when in fact he is controlling (i.e. moving) another tool outside the field of view, potentially damaging tissue.

Likewise, one advantage, for example, of predicting the position and orientation of the tool, and erasing or brushing out the shaft of the tool while highlighting its end effector in some fashion so that the end effector seemingly floats in and stands out on the display screen, is that it makes more of the underlying tissue viewable by the surgeon. Note, however, that this view of the underlying tissue is by definition synthetic, as the current state of the tissue is obscured by the tool. To erase the tool shaft therefore requires storage of previous images of the operating site, such that the obscured region could be replaced with the last-known un-obscured view of that region, perhaps in a dimmed or grayed-out fashion (a.k.a. Fog-of-War), to indicate that the data is not current.

Tool tracking refers to the determination of a tool's state over time. The tool's state generally includes its position and orientation in a reference frame, as well as other related parameters such as its translational and rotational velocities. In the preferred embodiment, tool tracking is performed in the camera reference frame. Tool tracking facilitates prediction of the tool's position and orientation at a point in time when the tool is either out of view or occluded in the endoscope's view, by using position and orientation information from prior times when the tool was in view and identifiable, and/or position and orientation estimates derived from non-endoscope sources for that point in time and previous times.

Determination of the position and orientation of the tool is useful for reasons other than locating the tool on the workstation display screen. For example, tool position and orientation information may be used to generate graphical overlays containing information of interest to the surgeon. These overlays might include: telestration, the distance between tools, the distance between tools and the patient's anatomy, measurements of anatomical features in the camera reference frame, or measurements of anatomical features in another reference frame. Additionally, the position and orientation of the tool may be used to register the current tool and camera positions with pre-operative or planning data provided in a fixed or world reference frame, or to improve in general the safety and control of robotic mechanisms manipulating the tools.

As yet another example, determination of the position and orientation of the tool is also useful for the registration of data collected during a surgical procedure from sensors mounted on the tools themselves, for example, ultrasound sensors. In this case, if the position and orientation of the tool holding the sensor is known in the camera reference frame (i.e., the reference frame of the endoscope), then the position and orientation of any data collected from a ultrasound sensor mounted on the tool could be displayed, fully registered with the surgical image, on the workstation display screen to aid the surgeon during the surgical procedure.

In certain of these registration examples, it is necessary to determine the position and orientation of the tool in the fixed (or world) reference frame. Therefore, if the position and orientation of the endoscope is known in the fixed reference frame, then the position and orientation of the tool as viewed by the endoscope can be translated from the camera reference frame to the fixed reference frame. Alternatively, if the position and orientation of the tool can be determined in the fixed reference frame independently, the independent determination not only avoids this reference frame translation process, but it also provides an alternative means to determine the endoscope's position and orientation in the fixed reference frame.

Accordingly, it is an object of aspects of the present invention to provide a method and system for performing tool tracking during minimally invasive surgery that operates even when a portion or even the entire tool is occluded in or out of the endoscope's view.

Another object of aspects of the invention is to provide a method and system for performing tool tracking that includes visual tracking using a marker that is orientation dependent so that a pose of the tool can be determined.

Another object of aspects of the invention is to provide a method and system for performing tool tracking that is accurate, reliable and/or computationally fast.

Still another object of aspects of the invention is to provide a method and system for performing tool tracking that operates real-time and minimizes abrupt transitions in determined tool positions and orientations so as to provide smooth tracking of the tool.

Yet another object of aspects of the invention is to provide a method and system for performing tool tracking that corrects or otherwise compensates for calibration errors.

These and additional objects are accomplished by the various aspects of the present invention, wherein briefly stated, one aspect is a tool tracking method comprising: tracking a tool by processing non-endoscopically derived tool state information and endoscopically derived tool state information generated while the tool is inserted and being manipulated through a minimally invasive incision in a body.

By using such a hybrid approach, when the tool is totally occluded in a frame of video from an endoscope inserted in the patient's body to view the surgical site, its state (e.g., its position, orientation, and translational and rotational velocity) may still be determined from the non-endoscopically derived tool position information such as that generated by: using system kinematics from joint positions in a robotic mechanism that is manipulating the tool; using electromagnetic, acoustic, or other types of detectable signals emanating or reflecting from the tool (or the robotic mechanism manipulating the tool) so as to determine its position; using images generated by an external camera viewing an end of the tool extending out of the patient's body.

Also, the additional use of the non-endoscopically derived tool position information along with the endoscopically derived tool position information in determining tool position and orientation tends to minimize or at least significantly reduce any abrupt transitions in determined tool positions and orientations between frames of the image information provided the non-endoscopically derived tool position information is continuously available at a sampling rate. Further, the use of the endoscopically derived tool position information along with the non-endoscopically derived tool position information provides a redundant source of information for determining tool states, which can be utilized to determine more accurate tool tracking of tool positions and orientations over time.

Another aspect is a tool tracking method comprising: receiving sensor information indicative of a position and orientation of a tool when the tool is inserted through an incision in a body; receiving image information for the tool; and determining the position and orientation of the tool using both the sensor and the image information.

Another aspect is a minimally invasive robotic surgery system with tool tracking, comprising: one or more non-endoscopic devices providing data from which non-endoscopically derived tool state information is generated when a tool is inserted and robotically manipulated through an incision in a body; an endoscope capturing images from which endoscopically derived tool state information is generated for an area within the body when the tool is inserted therein; and a processor configured to process the non-endoscopically and endoscopically derived tool state information for tracking the state of the tool.

Another aspect is a minimally invasive robotic surgery system with tool tracking, comprising: one or more sensors providing sensor data from which non-visually derived tool state information for a tool is generated when the tool is inserted and robotically manipulated through an incision in a body; at least one camera capturing image information of the tool when the tool is inserted therein; and a processor configured to process the non-visually derived tool state information and the image information for tracking the state of the tool.

Another aspect is a tool tracking method comprising: determining a computer model of a tool; receiving a captured image including a view of the tool; determining an estimated position and orientation of the tool from the captured image, and positioning and orienting the computer model at that estimated position and orientation in reference to the captured image; and modifying the estimated position and orientation of the computer model with respect to an image of the tool in the captured image until the computer model approximately overlays the image so as to correct the estimated position and orientation of the tool for the captured image.

Another aspect is a tool tracking method comprising: determining whether sensor data indicative of a tool state is available for a point in time; determining whether image data indicative of the tool state is available for the point in time; and determining the tool state using both the sensor data and the image data if both are available for the point in time, or using only the sensor data if only the sensor data is available, or using only the image data if only the image data is available.

Another aspect is a tool tracking method comprising: determining a first estimated tool state relative to a landmark for a point in time using first sensor data indicative of the tool state at the point in time; determining an estimated camera state relative to the landmark for the point in time using second sensor data indicative of the camera state at the point in time; determining a second estimated tool state relative to the camera for the point in time using image data generated by the camera and indicative of the tool state at the point in time; translating the first estimated tool state so as to be relative to the camera instead of the landmark; and computing an error transform between the first and the second estimated tool states so that at a subsequent point in time if image data indicative of the tool state at the subsequent point in time is not available, then the tool state is determined by applying the error transform to a third estimated tool state determined using sensor data indicative of the tool state at the subsequent point in time translated so as to be relative to the camera instead of the landmark.

Still another aspect is a tool tracking method comprising: determining non-endoscopically derived estimated state information for a tool at a given time; determining endoscopically derived estimated state information for the tool at the given time; and providing the non-endoscopically derived estimated state information and the endoscopically derived estimated state information to a Bayesian filter configured so as to generate an optimal estimate of the state of the tool.

Another aspect is a tool tracking and calibration method comprising: generating visually derived state information from image data received from a camera viewing a tool; generating state vector information by combining initial values for a set of camera parameters with the visually derived state information; and providing the state vector information to a Bayesian filter for processing so as to generate an optimal estimate of a state of the tool and corrected values for the set of camera parameters.

Another aspect is a camera tracking method comprising: determining a position of a tool in a fixed reference frame from non-visually derived tool state information generated from sensor data indicative of the position of the tool; determining a position of the tool in a camera frame moveable with a camera using visually derived tool state information generated from image data provided by the camera while viewing the tool; and determining a position of the camera in the fixed reference frame using the position of the tool in the fixed reference frame and the position of the tool in the moveable camera frame.

Another aspect is a tool tracking method comprising: determining a position of a camera in a fixed reference frame from non-visually derived camera state information generated from sensor data indicative of the position of the camera; determining a position of a tool in a camera frame moveable with the camera using visually derived tool state information generated from image data provided by the camera while viewing the tool; and determining a position of the tool in the fixed reference frame using the position of the camera in the fixed reference frame and the position of the tool in the moveable camera frame.

Still another aspect is a tool tracking method comprising: generating a plurality of estimated tool states for each point in a plurality of points in time, while the tool is inserted and being manipulated through an incision in a body; and determining an optimal estimated tool state for each point in the plurality of points in time by processing the plurality of estimated tool states using Bayesian techniques.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
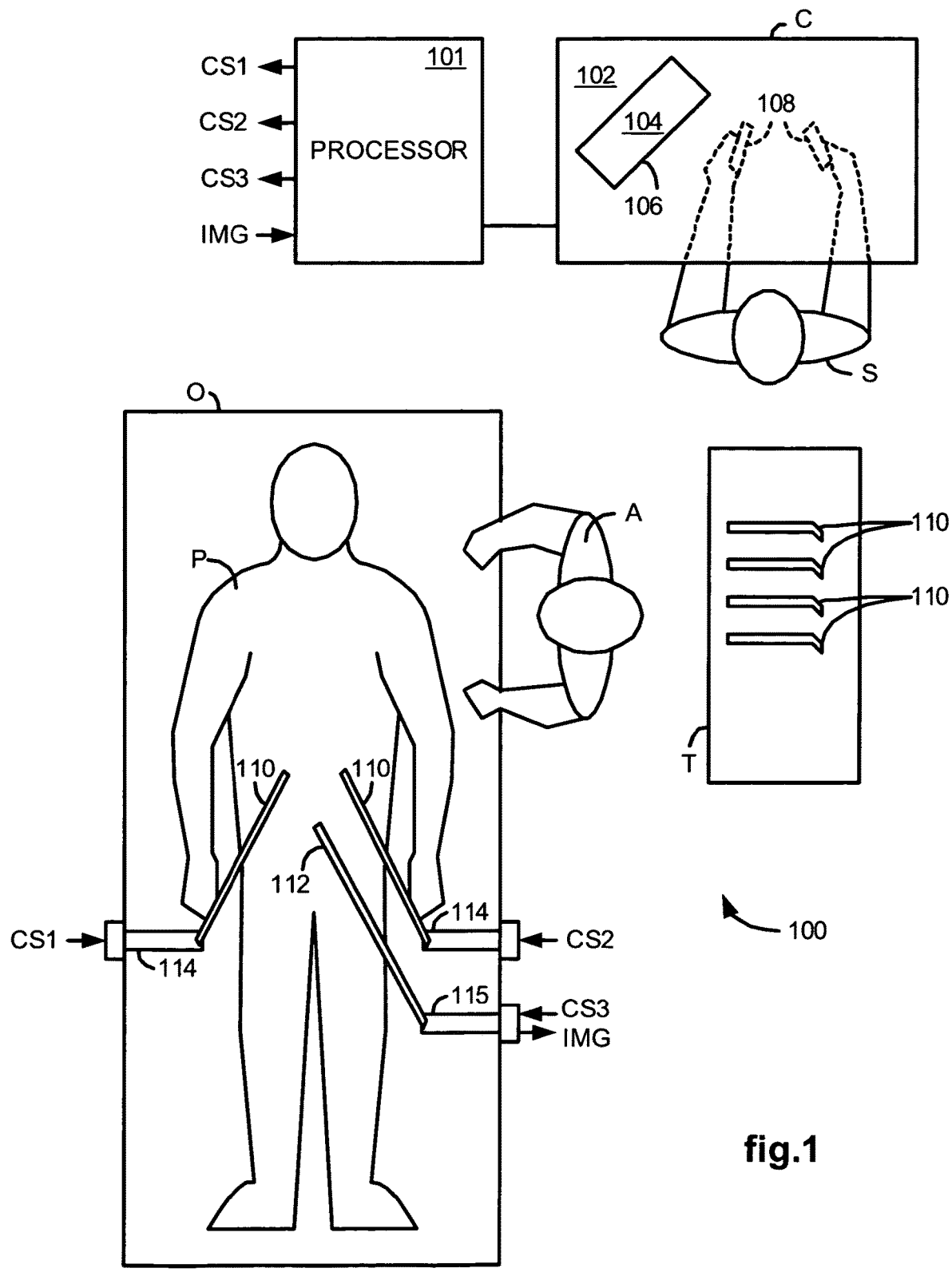
FIG. 1 illustrates a minimally invasive robotic surgical system utilizing aspects of the present invention.

FIG. 1 illustrates, as an example, a Minimally Invasive Robotic Surgical (MIRS) system 100 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a support 102, a monitor 104 for displaying an image of a surgical site to the Surgeon, and one or more control devices 108. The control devices 108 may include any one or more of a variety of input devices, such as joysticks, gloves, trigger-guns, hand-operated controllers, voice recognition devices or the like.

The Surgeon performs a procedure by manipulating the control devices 108 which in turn, cause robotic mechanisms 114 to manipulate their respective removably coupled instrument or tool assembly 110 (hereinafter simply referred to as a "tool") through a minimally invasive incision in the body of the Patient while the Surgeon views the surgical site through the monitor 104. The number of surgical tools 110 used at one time and consequently, the number of robotic mechanisms 114 in the system 100 will generally depend on the diagnostic or surgical procedure and the space constraints within the operating room among other factors. If it is necessary to change one or more of the tools 110 being used during a procedure, the Assistant may remove the tool 110 no longer being used at the time from its robotic mechanism 114, and replace it with another tool 110 from a tray ("T") in the operating room.

The surgeon's Console is usually located in the same room as the Patient so that the Surgeon may directly monitor the procedure, be physically available if necessary, and speak to the Assistant directly rather than over the telephone or other communication medium. However, it will be understood that the Surgeon can also be located in a different room, a completely different building, or other remote location from the Patient allowing for remote surgical procedures.

Preferably, control devices 108 will be provided with the same degrees of freedom as their associated tools 110 to provide the Surgeon with telepresence, or the perception that the control devices 108 are integral with the tools 110 so that the Surgeon has a strong sense of directly controlling the tools 110. To this end, position, force, and tactile feedback sensors (not shown) are preferably employed on the tools 110 to transmit position, force, and tactile sensations from the tools 110 back to the Surgeon's hands as he/she operates the control devices 108.

Monitor 104 is suitably coupled to a viewing scope assembly 112, including one or more cameras, through a processor 101, and positioned on the support 102 of the Console such that an image of the surgical site is provided near the Surgeon's hands. Preferably, monitor 104 will display an inverted image on a display 106 that is oriented so that the surgeon feels that he or she is actually looking directly down onto the operating site. To that end, an image of the tools 110 appear to be located substantially where the operator's hands are located even though the observation points (i.e., the endoscope or viewing camera) may not be from the point of view of the image.

In addition, the real-time image is preferably transformed into a perspective image such that the operator can manipulate the end effector of a tool 110 through its corresponding control device 108 as if viewing the workspace in substantially true presence. By true presence, it is meant that the presentation of an image is a true perspective image simulating the viewpoint of an operator that is physically manipulating the tools 110. Thus, the processor 101 (or another processor in the Console) transforms the coordinates of the tools 110 to a perceived position so that the perspective image is the image that one would see if the viewing scope assembly 112 was located directly behind the tools 110.

The processor 101 performs various functions in the system 100. Preferably it is used to transfer the mechanical motion of control devices 108 to robotic mechanisms 114 connected to tools 110 via control signals such as CS1 and CS2. In addition, it is preferably used to perform a tool tracking method that in turn, may be used to control movement of the viewing scope assembly 112 through its robotic mechanism 115 via control signal CS3 so that it tracks one or more of the tools 110, as well as for other purposes such as those previously described. The processor 101 may be separate from or integrated as appropriate into the robotic mechanisms 114 and 115, or it may be integrated in whole or in part into the Console serving as its processor or a co-processor to its processor.

The processor 101 also preferably provides force and torque feedback from the tools 110 to the hand-operated control devices 108. In addition, it preferably performs a safety monitoring function that freezes or at least inhibits all robot motion in response to recognized conditions such as exertion of excessive force on the Patient or a "running away" of the robotic mechanisms 114 or 115.

Although described as a processor, it is to be appreciated that the processor 101 may be implemented in practice by any combination of hardware, software and firmware. Also, its functions as described herein may be performed by one unit, or divided up among different components, each of which may be implemented in turn by any combination of hardware, software and firmware.

Additional details of the general operation and structure of the system 100 with respect to its manipulation and control of tool 110 are described, as an example, in commonly owned U.S. Pat. No. 6,346,072 entitled "Multi-Component Telepresence System and Method," which is incorporated herein by this reference.

Figure 2:
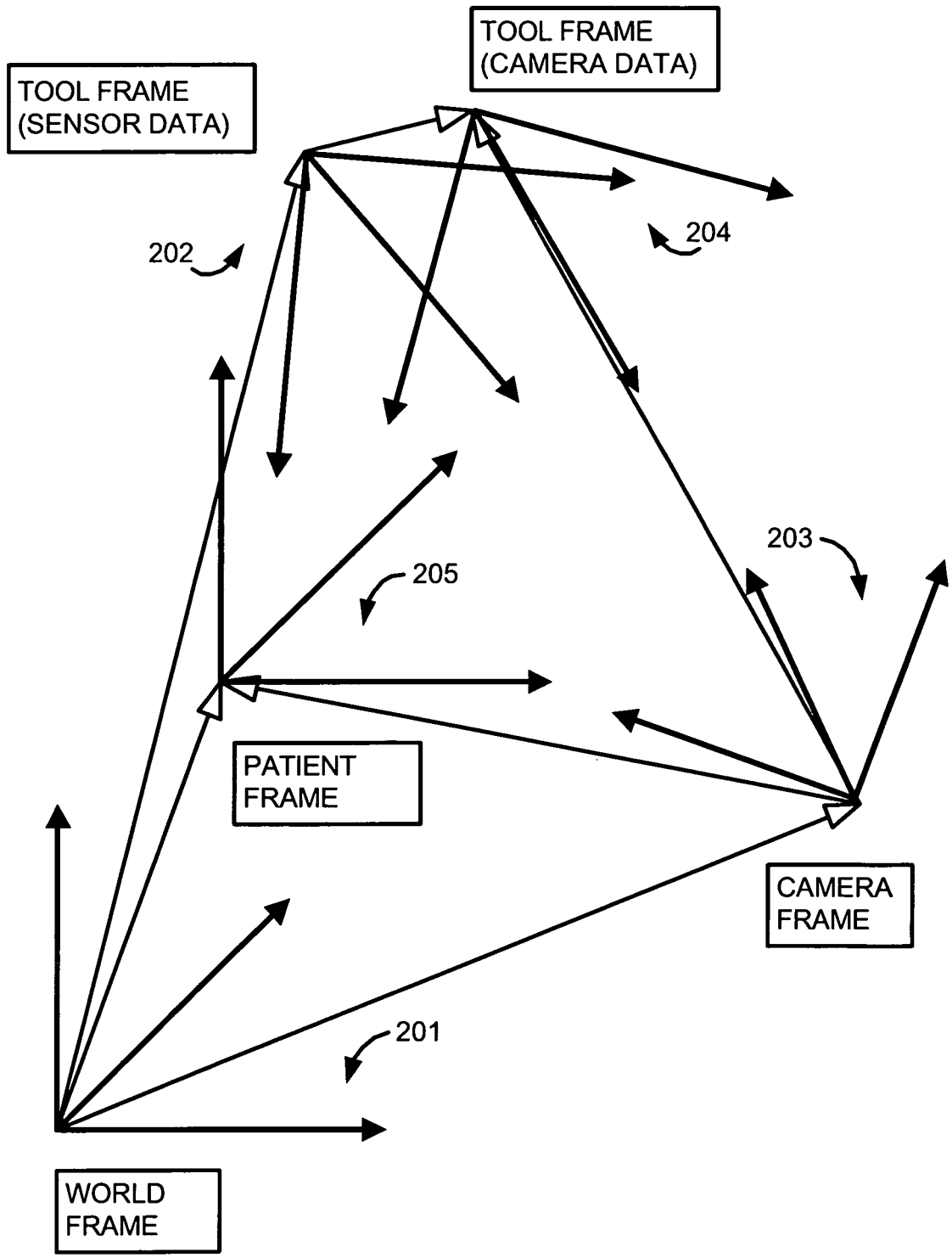
FIG. 2 illustrates three-dimensional reference frames associated with a minimally invasive robotic surgical system utilizing aspects of the present invention.

FIG. 2 illustrates, as examples, various reference frames associated with the MIRS system 100. A world reference frame 201 is a fixed reference frame centered, for example, at a fixed point (i.e., a landmark) in an operating room in which the minimally invasive diagnostic or surgical procedure is taking place. A tool reference frame 202, on the other hand, is a moving reference frame that is centered, for example, on a fixed point on the tool and consequently, moves with the tool. Similarly, a camera reference frame 203 is also a moving reference frame that is centered, for example, on a fixed point on a camera and consequently, moves with the camera. The position and orientation of the tool reference frame 202 and the camera reference frame 203 relative to the world reference frame 201 are preferably determined from sensor data associated with robotic mechanisms used to manipulate their respective positions and orientations.

Another tool reference frame 204 represents the position and orientation of the tool reference frame as determined from the camera frame 203. In the absence of systematic errors, tool reference frames 202 and 204 would exactly coincide. A patient reference frame 205, is a semi-fixed reference frame that is centered, for example, on a fixed point on the patient and consequently, moves along with that point if the patient moves.

The camera defining the camera reference frame 203 is preferably a stereo camera that is calibrated so that each pair of corresponding points in its left and right image planes is mapped to a three-dimensional point in its camera reference frame 203. The position of a tool as perceived by the camera (e.g., the tool reference frame 204) may then be determined, for example, by first identifying the tool in the left and right image planes of the camera, then using the calibration information to determine the position of the tool in the camera reference frame 203.

Generally, the camera reference frame 203 is associated with an endoscope inserted in the surgical site so as to be able to view the effector end of the tool during the surgical procedure. As indicated above, the endoscope in this case is preferably a stereoscopic endoscope. A second camera reference frame (not shown) may also be defined and associated with an external camera unit positioned outside of the patient, but in sufficiently close proximity so as to be able to view the rear end of the tool extending out of the patient during the surgical procedure. The external camera unit is also preferably a stereoscopic camera to facilitate 3-D determinations.

As previously described, both the tool and endoscope are preferably manipulated through incisions in the patient's body using robotic mechanisms. Each of these robotic mechanisms includes joints and linkages which allow movement of its respective tool or endoscope through five or six degrees of freedom.

The position and orientation of the tool (as depicted by the position and orientation of the tool reference frame 202) and endoscope (as depicted by the position and orientation of the camera reference frame 203) may be determined in the world reference frame 201 by attaching sensors to the joints and/or linkages of their respective robotic mechanisms to sense their movement. Such techniques are well known in robotics, along with the fact that their results depend upon the particular construction and operation of the robotic mechanism. Additional details may be found, for example, in John J. Craig, "Introduction to Robotics—Mechanics and Control," 2nd Ed., Addison Wesley Longman, 1986.

Another method for determining the tool and endoscope positions and orientations in the world reference frame 201 include sensing electromagnetic, acoustic, or other identifiable signals emanating or being reflected from the tool or endoscope so as to indicate its position and orientation. Still another method for determining the tool and endoscope positions and orientations in the world reference frame 201 include the use of the external stereoscopic camera described above, which may view the rear ends of the tool and endoscope extending out of the patient's body and determine its position and orientation through calculations based upon its left and right image planes.

By determining the positions and orientations of the endoscope (as depicted by the camera reference frame 203) and tool (as depicted by the tool reference frame 202) determined by sensors in the world reference frame 201, the determination of the tool position and orientation in the world reference frame 201 can be checked using conventional triangulation techniques employing the endoscope position and orientation determined in the world reference frame 201 along with the tool position and orientation (as depicted by the tool reference frame 204) determined in the camera reference frame 203 of the endoscope. Conversely, the determination of the endoscope position and orientation (as depicted by the camera reference frame 203) in the world reference frame 201 can be checked using conventional triangulation techniques employing the tool position and orientation (as depicted by the tool reference frame 202) determined in the world reference frame 201 along with the tool position and orientation (as depicted by the tool reference frame 204) determined in the camera reference frame 203 of the endoscope. Having additional means for determining the tool and endoscope positions and orientations provide still more ways to check their respective positions and orientations and provide more accurate determinations.

Figure 3:
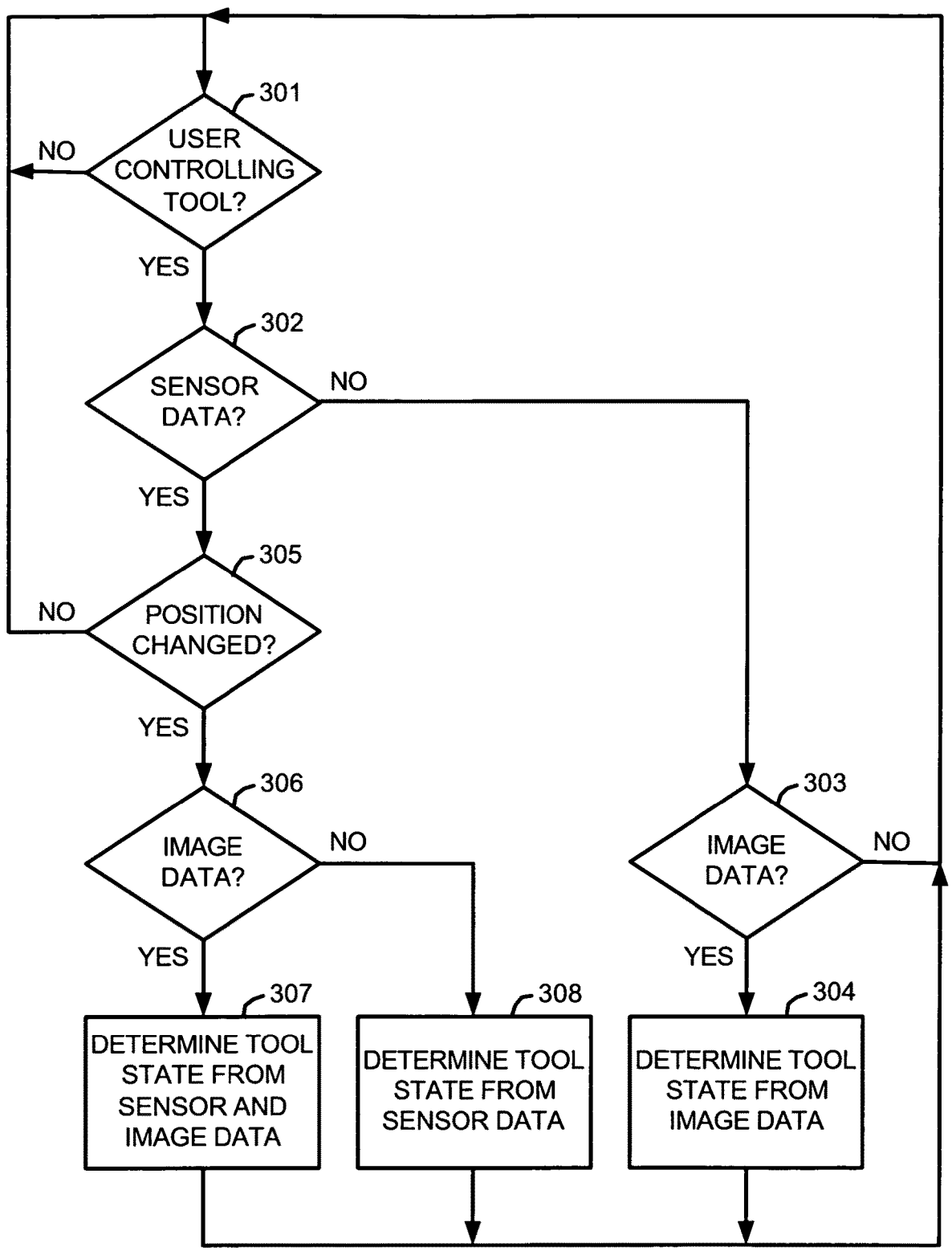
FIG. 3 illustrates a flow diagram of a tool tracking method for determining tool states using either or both tool sensor and tool images data, utilizing aspects of the present invention.

FIG. 3 illustrates, as an example, a flow diagram of a tool tracking method that tracks a tool by processing available sensor and image data of the tool, which were generated while the tool is inserted and being manipulated through a minimally invasive incision in a body. The sensor data in this case is from position sensors such as those employed for detecting joint positions in a robotic mechanism manipulating the tool, or those employed for detecting electromagnetic, acoustic, or other identifiable signals emanating or being reflected from the tool to indicate its position. In order to properly process the data together, both sensor and image data are preferably time stamped in some manner so that data associated with the same points in time can be processed with each other.

In 301, a determination is made whether a tool is currently under the active control of a user, for example, by the corresponding control device being turned on by the user. If the determination in 301 is NO, then the method keeps periodically looping through 301 until the determination in 301 results in a YES, at which time, in 302, a determination is then made whether sensor data indicating the tool's state is available. If the determination in 302 is NO, then in 303, a determination is made whether image data indicating the tool's state is available. If the determination in 303 is also NO, then no information is available for determining the tool's state at this time, and the method jumps back to 301 to start the process over again at another time. On the other hand, if the determination in 303 is YES, then in 304, the state of the tool is determined using only the image data at this time, and following such determination, the method jumps back to 301 to restart the process for another time.

If the determination in 302 is YES, however, indicating that sensor data is available, then in 305, a determination is made whether the position of the tool has changed since its last determination. It is advantageous to perform this determination at this time, because the determination is relatively easy and fast to perform, and if the tool hasn't moved, it avoids unnecessary computation to determine the new tool position and orientation.

As an example of one technique for performing the determination in 305: (i) joint velocities are determined from sensors employed on the joints of the robotic mechanism that is manipulating the tool, (ii) the joint velocities are each squared, (iii) the squared joint velocities are summed together, and (iv) the resulting value is compared against a threshold value so that the tool is determined to have moved only if the resulting value is greater than the threshold value.

If the determination in 305 is NO, then the method jumps back to 301 to start the process over again at another time. On the other hand, if the determination in 305 is YES, then in 306, a determination is made whether image data indicating the tool's state is available. If the determination in 306 is NO, then in 308, the state of the tool is determined using only the sensor data at this time, and following such determination, the method then jumps back to 301 to restart the process at another time. However, if the determination in 306 is YES, then in 307, the state of the tool is determined using both the sensor and image data at this time, and following such determination, the method then jumps back to 301 to restart the process for another time.

In the method described above in reference to FIG. 3, there is no assumption made regarding the availability of either the sensor or image data. Therefore, the method described therein checks independently whether both types of data are available and determines the tool's position accordingly. Although the availability of sensor data is checked before checking the availability of image data in this method, it is to be appreciated that this checking procedure can be reversed and still be within the scope of this aspect of the present invention.

The sensor data may be received from sensors or encoders positioned on joints and/or linkages on the robotic mechanism manipulating the tool during a surgical procedure, or the sensor data may be received from sensors detecting electromagnetic, acoustic, or other identifiable signals emanating or being reflected from the tool so as to indicate its position. The image data may be received from an endoscope viewing the effector end of the tool within the patient's body, or the image data may be received from an external camera viewing the exposed end of the tool extending outside of the patient's body during the surgical procedure.

Figure 4:
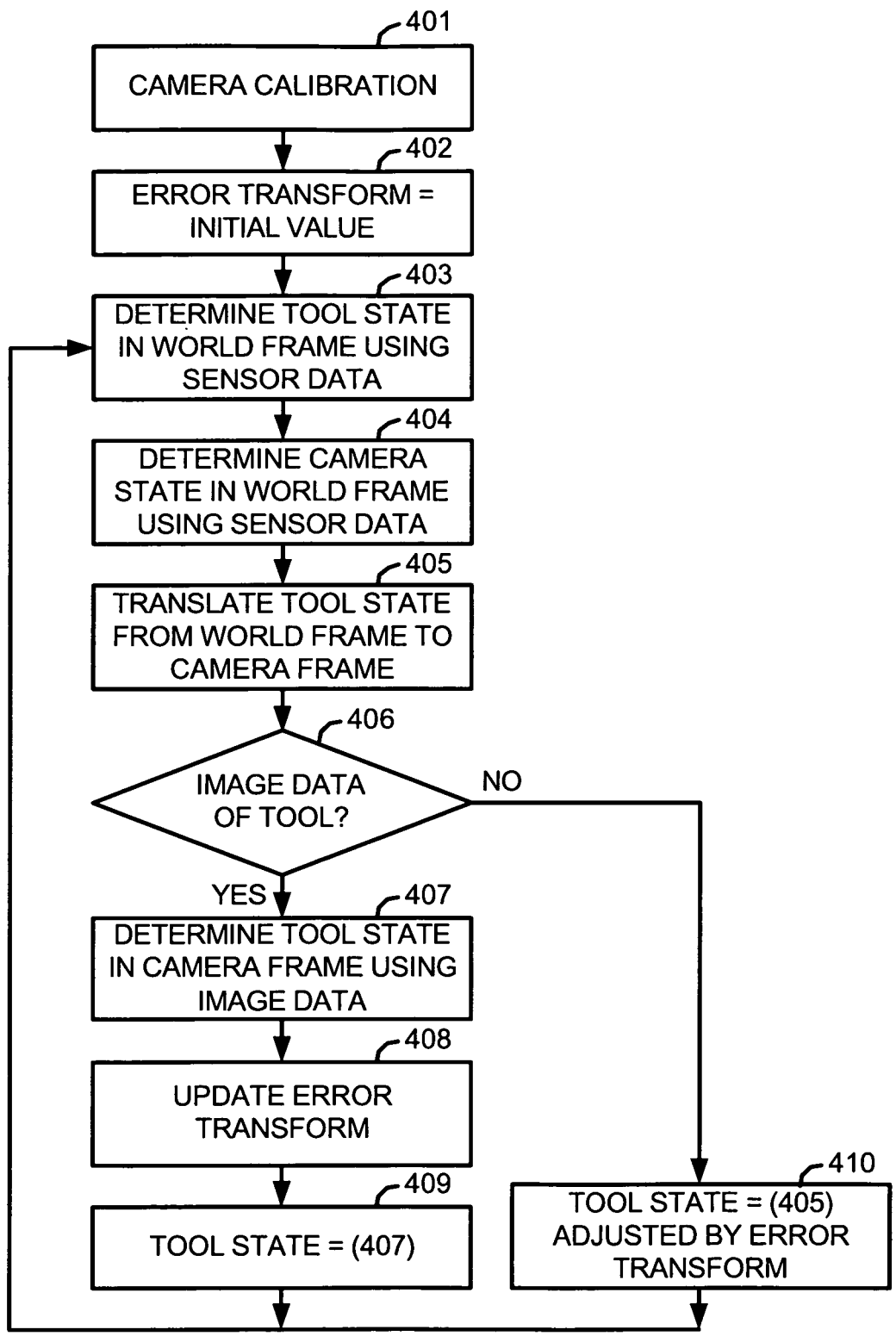
FIG. 4 illustrates a flow diagram of a tool tracking method for determining tool states using both tool sensor and tool images data, utilizing aspects of the present invention.

FIG. 4 illustrates, as an example, a tool tracking method for determining tool states using both tool sensor and available tool image data. In the method, 401 and 402 are generally performed off-line prior to a surgical procedure, and 403-410 are performed on-line during the surgical procedure.

In 401, a stereoscopic endoscope is calibrated off-line so that mapping of points may be performed between its left and right 2-D image planes and the 3-D camera frame 203. Calibration in this case includes determining the intrinsic camera parameters such as the focal length (e.g., see length "F" in FIG. 6), principal point, skew, and distortion for each camera of the stereo pair. Additionally, the rotation and translation between the two cameras in the stereo pair may be determined.

Camera calibration may be performed once such as during the initial set-up of the MIRS system 100, or it may be performed periodically such as just prior to performing a minimally invasive diagnostic or surgical procedure. One technique for performing the calibration is to capture several images of a calibration grid in a variety of positions and orientations. These images may then be fed into a commercially available (or home grown) calibration package that extracts the corner positions in the images of the calibration grid, and performs a calibration/optimization procedure to obtain the required parameters.

In 402, initial values for error transforms are determined at the start of each surgical procedure. The error transform is defined as the position and orientation of a second estimated tool state (such as depicted as the tool reference frame 204) determined in the camera reference frame 203 from left and right image planes of the stereoscopic camera, in the reference frame of a first estimated tool state (such as depicted as the tool reference frame 202) determined in the world reference frame 201 from sensor data and translated to the camera reference frame 203 of a stereoscopic camera. Following the transform notation defined in "Introduction to Robotics—Mechanics and Control" previously referenced, this may be represented as $$^{202}_{204}T.$$

This procedure begins, for example, by applying an initial translation to the tool location from sensor data such that the perspective projection of this translated tool location is centered in the left and right images. The user then moves the tool to the four corners of the stereoscopic images and clicks on the 2D tool locations in both left and right images. Combining the initial translation, the tool's 3-D sensor locations, and the tool's 2-D image locations, gives an initial value of the error transform $$^{202}_{204}T$$

between the tool location (such as depicted as the tool reference frame 202) as determined from the sensors and the tool location (such as depicted as the tool reference frame 204) as determined from the stereoscopic image. After their determinations, the initial values are loaded into short-term memory just prior to initiating 403-410.

In 403, the tool state in the world reference frame 201 is determined from the sensor data. For the nominal case when the tool state consists only of position and orientation, this may be represented as the transform $$^{201}_{202}T$$

(see "Introduction to Robotics—Mechanics and Control," for details). This may be determined, for example, from system kinematics using data provided from joint or linkage position sensors associated with a robotic mechanism manipulating the tool, or by calculating the tool position in the world reference frame 201 using signals emanating or being reflected back from the tool indicating its position. Although both examples provide state information, the use of system kinematics is preferable for performing this function, because it generally provides more tool state information than the tool position indicating signals.

In 404, the camera state in the world reference frame 201 is also determined from the sensor data. For the nominal case when the tool state consists only of position and orientation, this may be represented as the transform $$^{201}_{203}T$$

(see "Introduction to Robotics—Mechanics and Control," for details). As in the case of the tool state determination in 403, this may be determined, for example, from system kinematics using data provided from joint or linkage position sensors associated with a robotic mechanism manipulating the camera, or by calculating the camera position in the world reference frame 201 using signals emanating or being reflected back from the camera indicating its position.

In 405, the estimated tool state determined in 403 is translated from the world reference frame 201 to the camera reference frame 203 of the camera using conventional reference frame transformation techniques using the estimated camera state (in the world reference frame 201) determined in 404.

$$^{203}_{202}T = ^{201}_{203}T^{-1}\, ^{201}_{202}T \qquad (1)$$

In 406, a determination is made whether image data of the tool is available for the corresponding point in time that the tool state was determined in 403. The image data may not be available if either an image was not captured by the camera for the corresponding point in time, or the tool is not identifiable in an image captured by the camera for the corresponding point in time. The latter case may happen as the tool moves in and out of the camera's view due to manipulation of the tool by the surgeon during the surgical procedure. To assist with identifying tools in a captured image, various tool identification techniques may be used, including the use of special markers as described herein.

As a refinement to the above, even if the tool is identifiable in the image data, it may be identified as an outlier and therefore, rejected if its state falls outside of a tolerance range of a best fit curve generated from previously determined tool states at prior time points.

If the determination in 406 is YES, then in 407, an estimate of the tool state (such as depicted as the tool reference frame 204) in the camera reference frame 203 is determined directly. For the nominal case when the tool state consists only of position and orientation, this may be represented as the transform $$^{203}_{204}T.$$

As an example of one technique for performing this task, a control point is identified on the tool in both the left and right 2-D image planes received from the stereoscopic camera, then the corresponding location of that point in the 3-D camera reference frame 203 using the previously generated calibration data is determined.

As an example of how the control point may be identified in the two image planes, a small window including the control point may be selected in the left image, and cross correlated with small windows in the right image to determine a window in that image with a highest correlation factor, which results in a match and identification of the control point in that image.

After determining the tool state in 407, a revised error transform $$^{202}_{204}T$$

is calculated in 408 as the transform between the tool state determined in 405 and the tool state determined in 407, and stored in the short-term memory replacing any initial value stored therein. The estimated tool state determined in 407 is then determined in 409 to be the tool state for that point in time. The method then jumps back to 403 to determine the tool state in the camera reference frame 203 for another point in time.

$$^{202}_{204}T = ^{203}_{202}T^{-1}\, ^{203}_{204}T \qquad (2)$$

On the other hand, if the determination in 406 is NO, then in 410, the tool state (such as depicted as the tool reference frame 204) in the camera reference frame 203 is then determined to be the estimated tool state determined in 405 adjusted by the error transform corresponding to that tool state as determined in 402. In this case, the error transform is not updated. The method then jumps back to 403 to determine the tool state in the camera reference frame 203 for another point in time.

$$^{203}_{204}T = ^{203}_{202}T\, ^{202}_{204}T \qquad (3)$$

Note that the error transforms may be updated during the surgical procedure in performing task 408, because the error transforms may slowly drift over time due to a variety of factors such as errors in the initial error transform estimate, initial correlation, system kinematics, or camera calibration, as well as other factors such as external forces applied to the tool or its manipulating robotic mechanism, or hysteresis or other non-linearities in the robotic mechanism.

Figure 5:
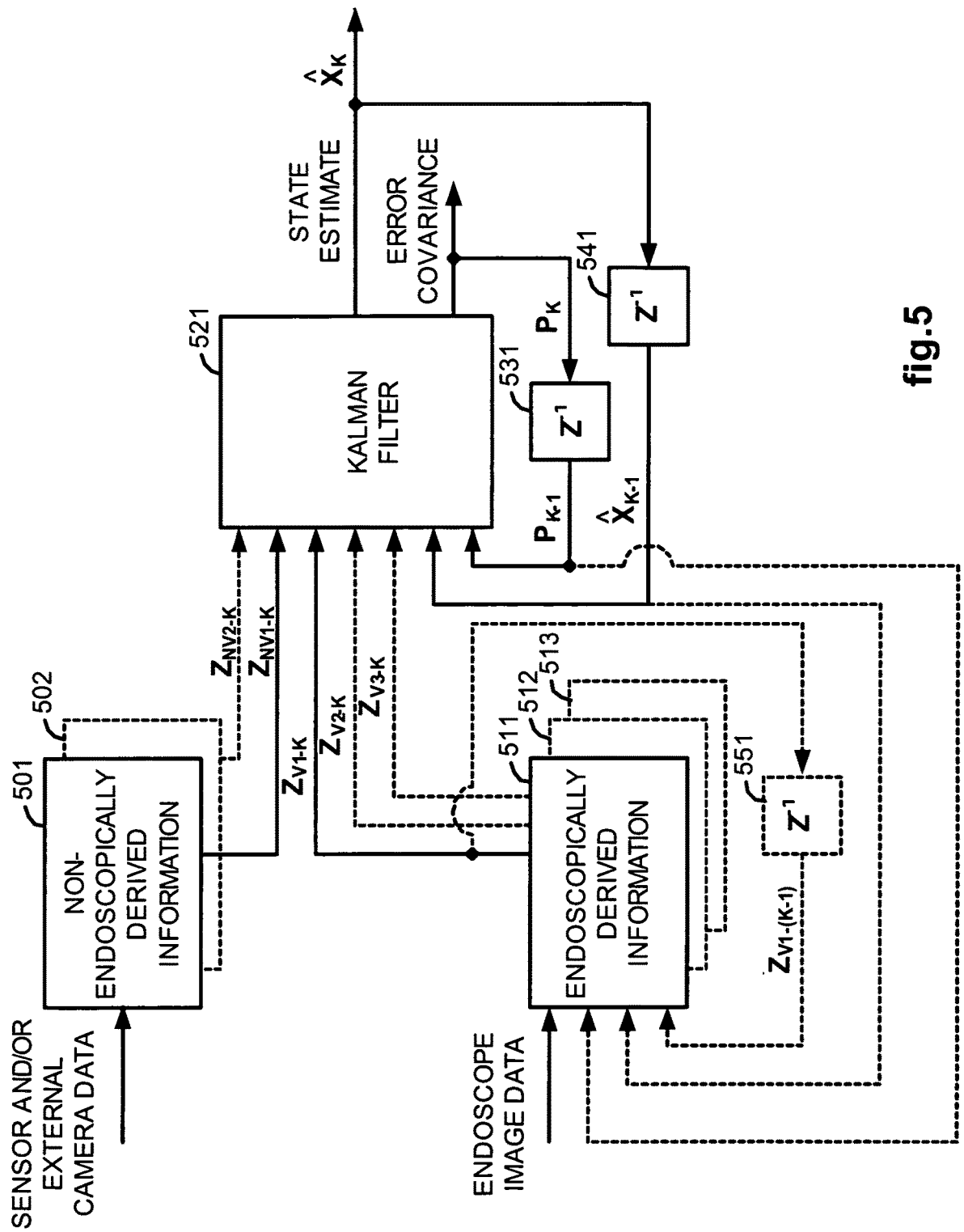
FIG. 5 illustrates a functional block diagram of a Kalman filter tool tracking method for determining tool states, utilizing aspects of the present invention.

FIG. 5 illustrates, as an example, a functional block diagram for an alternative tool tracking method. The tool tracking method in this case employs an Extended Kalman Filter ("EKF"), which has the purpose of producing an optimal estimate of the state of the tool being tracked, $\hat{x}_k$, by combining one or more non-endoscopically derived tool state information, e.g., $z_{NV1\text{-}k}$ and $z_{NV2\text{-}k}$ (respectively generated in blocks 501 and 502, by processing sensor and/or external camera data associated with the tool) with one or more endoscopically derived tool state information, such as $z_{V1\text{-}k}$, $z_{V2\text{-}k}$, and $z_{V3\text{-}k}$ (respectively generated in blocks 511, 512, and 513, by processing image data of the tool received from a stereoscopic endoscope using corresponding vision algorithms), and using a model of the system dynamics.

In this method, determinations of whether or not non-endoscopically derived or endoscopically-derived tool state information are available are not necessary (such as performed in 302 and 306 in FIG. 3 for sensor data and image data), because if either type of information is unavailable for the time of computation, this fact is simply taken into account by the unavailable information consisting of measurement values remaining at a previous value (i.e., not being updated at the time). For this and other reasons, the method described in reference to FIG. 5 is considered a preferred technique for determining tool states.

Note that although an EKF is used in this example, other Bayesian filters or techniques such as a Kalman Filter or Particle Filter may also be employed and are fully contemplated to be within the scope of the present invention. A Bayesian filter refers to a family of statistical filters based on Bayesian estimation techniques.

Also, note that all inputs referred to as sensor data, external camera data, or endoscopic image data may be thought of as measurements, wherein the quantity being measured is some subset of the tool state (typically position and orientation) in the corresponding sensor, external camera or endoscope reference frame. In general, all the sensor measurements of the tool state include some amount of processing such as a forward kinematics computation is generally required to compute the tool state from the robot joint position sensors. Further, all measurements are generally asynchronous, but referred to an absolute clock by a time stamp.

Each measurement is generally corrupted by some random error, such as zero mean noise, and can be either unavailable at some point in time (missing) or can be totally erroneous (outlier). The EKF thus reduces the effect of the measurement noise on the tool state estimate. The nominal transformation between each sensor, external camera or endoscope reference frame is used to fuse the measurements.

Function block 501 generates non-endoscopically derived tool state information, $z_{NV1-k}$, from sensor data, and provides the non-endoscopically derived tool state information to the EKF 521 for processing. As previously described, the non-endoscopically derived tool state information may be from joint position sensors, tool position signal detectors, or external cameras. Additional function blocks, such as function block 502, may optionally be included to generate additional non-endoscopically derived tool state information, such as $z_{NV2-k}$, from the same or other sensor data or external camera, and provide the additional non-endoscopically derived tool state information to the EKF 521 for processing.

On the other hand, function block 511 generates endoscopically derived tool state information, $z_{V1-k}$, from endoscope image data, and provides the endoscopically derived tool state information to the EKF 521 for processing. As previously described, the endoscope image data may be the left and right image planes from a stereoscopic endoscope. Additional function blocks, such as function blocks 512 and 513, may optionally be included to generate additional endoscopically derived tool state information, such as $z_{V2-k}$ and $z_{V2-k}$, generally from the same endoscope image data, and provide the additional endoscopically derived tool state information to the EKF 521 for processing.

The function blocks 501-502 and 511-513 perform some common tasks, as well as their individual special processing to generate their respective tool state information. As an example, each of the function blocks keeps track of time stamps placed on its received sensor or image data, which indicates when the data was sensed or captured, so that all tool state information provided by the function blocks at any given time to the EKF 521 corresponds approximately to the same time indicated on the time stamps. As another example, each of the function blocks preferably filters noise in its received sensor or image data so that the tool state information provided to the EKF 521 has approximately zero mean noise.

Following is a simplified example of how the EKF 521 is used for tool tracking during a minimally invasive diagnostic or surgery procedure. For a more thorough description of the EKF in general, see, for example, Greg Welch and Gary Bishop, "An Introduction to the Kalman Filter," TR 95-041, Department of Computer Science, University of North Carolina at Chapel Hill, Apr. 5, 2004.

As is well known, the EKF framework has two distinct phases, termed the "Time Update" (or "Predict") phase and the "Measurement Update" (or "Correct") phase.

In a first phase of the Kalman filter update cycle, the state estimate from the previous iteration of the filter is used to produce a prediction of the new state estimate for this cycle, $\hat{x}_k^-$, based on a (potentially) nonlinear model of the system dynamics, $f$, and a forcing function, $u_{k-1}$, according to equation (4) as follows:

$$\hat{x}_k^- = f(\hat{x}_{k-1}, u_{k-1}, 0) \qquad (4)$$

wherein the '0' in equation (4) is the process noise estimate used in producing the predicted state estimate.

Linearizing the nonlinear system model, $f$, about the point $\hat{x}_{k-1}$, the linearized state transition matrix, A, is obtained. Then, using the error covariance matrix from the previous iteration of the filter, $P_{k-1}$, a prediction of the new error covariance matrix is produced for this cycle, $P_k^-$, according to equation (5) as follows:

$$P_k^- = A_k P_{k-1} A_k^T + W_k Q_{k-1} W_k^T \qquad (5)$$

wherein the matrix W represents the Jacobian of the system dynamics with respect to the process noise, w, and Q is a tunable gain matrix.

Thinking physically, if the matrix P describes an error ellipse having a number of dimensions equal to the system state order, then by applying equation (5), the size of the error ellipse may be expanded using our model of the system dynamics encoded in the linearized state transition matrix, A, and the scaled estimate of the process noise, which represents uncertainty in the system dynamics model. Increasing the size of the error ellipse is equivalent to stating that there is greater uncertainty in the estimate of the system state.

In the second phase of the Kalman filter update cycle, the predicted state estimate and predicted error covariance matrix may be corrected by taking one or more measurements of the system.

The Kalman gain is then computed. The Kalman gain, in essence, weights the contributions from one or more measurements, such that their impact on the new state estimate reflects a current estimate of their reliability. Additionally, it allows weighting of the reliance on the model vs. the measurements. In other words, the contribution from a reliable measurement may be weighted more, and an unreliable measurement less. To do so, equation (6) is applied as follows.

$$K_k = P_k^- H_k^T (H_k P_k^- H_k^T + V_k R_k V_k^T)^{-1} \qquad (6)$$

To explain equation (6), it is first proposed that there is a function h, known as the measurement function, which relates the quantities that are able to be measured (observed) in the system, z, to the actual system state, x.

In equation (6), the estimate of the new error covariance matrix, $P_k^-$, from equation (5) is made use of. The matrix H is the Jacobian of the 'measurement' function, h, with respect to the system state, x. In essence, the H matrix describes how a change in the quantity being measured (observed), will change the actual system state.

The matrix V represents an estimate of the measurement noise, which includes both sensor noise, and uncertainty in the measurement function, h. The R matrix is a tunable gain.

Once the Kalman gain is computed according to equation (6), the estimate of the system state may be updated, using the predicted system state estimate, $\hat{x}_k^-$, and the measurements. In this case, the predicted system state estimate is adjusted by the Kalman-gain-weighted error between the actual measurement, $z_k$, and the predicted measurement, $\hat{z}_k$, according to equation (7) as follows.

$$\hat{x}_k = \hat{x}_k^- + K_k(z_k - h(\hat{x}_k^-, 0)) \tag{7}$$

Finally, the estimate of the error covariance is updated according to equation (8) as follows.

$$P_k = (I - K_k H_k) P_k^- \tag{8}$$

The value of $P_k$ should decrease at a rate proportional to the degree to which the measurements are trusted vs. the predictions. Physically, this implies that the error ellipse enclosing the system state estimate shrinks as additional measurements are obtained.

Now that the EKF framework has been described, its formulation with respect to the present application is detailed. In particular, the system state, x, the system state function, ƒ, the state transition matrix, A, the measurements, z, the measurement functions, h, and the measurement Jacobians, H, are defined.

The state of the system is the position, orientation, translational velocity, and rotational velocity of the laparoscopic tool end effector, as shown in equation (9). In this way the state of a rotating rigid body is described.

$$x = [xyz\theta_x\theta_y\theta_z\theta_w \dot{x}\dot{y}\dot{z}\omega_x\omega_y\omega_z]_{13\times 1}^T \tag{9}$$

Note that the orientation of the end effector, Θ, is represented using quaternion notation, rather than as a rotation matrix. This facilitates a smooth integration of the angular velocity to obtain the new rigid body orientation, as required by the system state update equations.

For the system update function, ƒ, a rigid body in free-space is described, with no forcing function input. The state propagation is described by equation set (10). Note, however, that in the preferred embodiment, the velocities are pre-multiplied by the ΔT between samples to obtain position deltas, and simply added in equation (10).

Here, an assumption is made of no forcing function because the time step is very small, and any acceleration imparted to the rigid body can be modeled as noise in the system model.

$$x_k^- = \begin{bmatrix} \hat{x}_k^- = \hat{x}_{k-1} + \hat{\dot{x}}_{k-1}\Delta T \\ \hat{y}_k^- = \hat{y}_{k-1} + \hat{\dot{y}}_{k-1}\Delta T \\ \hat{z}_k^- = \hat{z}_{k-1} + \hat{\dot{z}}_{k-1}\Delta T \\ \hat{\Theta}_k^- \\ \hat{\dot{x}}_k^- = \hat{\dot{x}}_{k-1} \\ \hat{\dot{y}}_k^- = \hat{\dot{y}}_{k-1} \\ \hat{\dot{z}}_k^- = \hat{\dot{z}}_{k-1} \\ \hat{\omega}_{x_k}^- = \hat{\omega}_{x_{k-1}} \\ \hat{\omega}_{y_k}^- = \hat{\omega}_{y_{k-1}} \\ \hat{\omega}_{z_k}^- = \hat{\omega}_{z_{k-1}} \end{bmatrix}_{13\times 1} \tag{10}$$

The state propagation for the orientation state, Θ, is a bit more complicated due to the use of quaternions. First, the quaternion derivative, which is a function of the current orientation and the angular velocity, is computed. To do so, the angular velocity quaternion, $q_1$, and the orientation quaternion, $q_2$, are described as shown in equation set (11).

$$q_1 = [\hat{\omega}_{x_{k-1}} \hat{\omega}_{y_{k-1}} \hat{\omega}_{z_{k-1}} 0]_{4\times 1}^T$$

$$q_2 = [\hat{\theta}_{x\ k-1} \hat{\theta}_{y\ k-1} \hat{\theta}_{z\ k-1} \hat{\theta}_{w\ k-1}]_{4\times 1}^T \tag{11}$$

The quaternion derivative is then calculated according to equation (12):

$$dq = \frac{1}{2} q_2 * q_1 \tag{12}$$

where the '*' operator denotes quaternion multiplication. Once the quaternion derivative has been computed, integration per equation (13) is performed.

$$\hat{\Theta}_k^- = \begin{bmatrix} \hat{\theta}_{x_{k-1}} + dq_x \Delta T \\ \hat{\theta}_{y_{k-1}} + dq_y \Delta T \\ \hat{\theta}_{z_{k-1}} + dq_z \Delta T \\ \hat{\theta}_{w_{k-1}} + dq_w \Delta T \end{bmatrix}_{4\times 1} \tag{13}$$

After integration, the resulting quaternion is enforced to be of unit length by normalizing $\hat{\Theta}_k^-$. Having defined the system state function, ƒ, equation (4) of the Kalman filter update cycle may be computed.

To satisfy equation (5) of the Kalman filter update cycle, the system state Jacobian matrix, A, must be defined. In the present case, if the above discussion is re-written in matrix form, the required matrix results as shown in equation (14).

$$A = \begin{bmatrix} I_{3\times 3} & 0_{3\times 4} & \Delta T \cdot I_{3\times 3} & 0_{3\times 3} \\ 0_{4\times 3} & A_q & 0_{4\times 3} & 0_{4\times 3} \\ 0_{3\times 3} & 0_{3\times 4} & I_{3\times 3} & 0_{3\times 3} \\ 0_{3\times 3} & 0_{3\times 4} & 0_{3\times 3} & I_{3\times 3} \end{bmatrix}_{13\times 13} \tag{14}$$

The matrix $0_{m\times n}$ is an m×n matrix of 0's. The matrix $A_q$, shown in equation (15), is the quaternion omega matrix, which encodes the quaternion multiplication operation, '*', described in equation (12).

$$A_q = \frac{1}{2} \begin{bmatrix} 0 & -\hat{\omega}_{z_{k-1}} & \hat{\omega}_{y_{k-1}} & \hat{\omega}_{x_{k-1}} \\ \hat{\omega}_{z_{k-1}} & 0 & -\hat{\omega}_{x_{k-1}} & \hat{\omega}_{y_{k-1}} \\ -\hat{\omega}_{y_{k-1}} & \hat{\omega}_{x_{k-1}} & 0 & \hat{\omega}_{z_{k-1}} \\ -\hat{\omega}_{x_{k-1}} & -\hat{\omega}_{y_{k-1}} & -\hat{\omega}_{z_{k-1}} & 0 \end{bmatrix}_{4\times 4} \tag{15}$$

Having defined the system state Jacobian matrix, A, equation (5) of the Kalman filter cycle update may now be computed.

In the present system, multiple measurement sources are provided. The first measurement as provided by function block 501, is in this case from the robot kinematics (encoders or position sensors), and is of the state directly, as shown in equation (16).

$$z_{NV1-k} = [xyz\theta_x\theta_y\theta_z\theta_w\dot{x}\dot{y}\dot{z}\omega_x\omega_y\omega_z]_{13\times 1}^T \tag{16}$$

Note that the end effector orientation has been converted from a rotation matrix to a quaternion, to fit within this framework. Also, note that in case the measurement from the robot kinematics is referred to a reference frame other than the camera reference frame of the endoscope, equation (16) would need to be modified so as to accommodate transformation to the camera reference frame.

The second measurement as provided by function 511 is obtained by processing the left and right images provided by the stereoscopic endoscope. The coordinates $(u_l, v_l)$ and $(u_r, v_r)$ are the position of the end-effector in the left and right image planes, respectively.

$$z_{V1-k} = [u_l, v_l, u_r, v_r]_{4 \times 1}^T \tag{17}$$

Before combining non-endoscopically derived tool state information and endoscopically derived tool state information according to equation (18) below, it is first useful to verify that the endoscopically derived estimates of tool state are not outliers.

Assuming that they are not outliers, to form the full measurement vector, the two measurements are then stacked as shown in equation (18).

$$z_k = \begin{bmatrix} z_{NV1-k} \\ z_{V1-k} \end{bmatrix}_{17 \times 1} \tag{18}$$

Note that additional non-endoscopic processing algorithms may be run, such as in block 502, each resulting in a set of measurements, such as $z_{NV2-k}$, and additional endoscopic processing algorithms on the endoscope images may be run, such as in blocks 512 and 513, each resulting in a set of measurements, such as $z_{V2-k}$ and $z_{V3-k}$, all of which may in turn be stacked in the measurement vector.

To satisfy equation (7) of the Kalman filter update cycle, the measurement functions, h, must be defined, which relate the system state x to the measured (observed) quantities, z.

As previously noted, there are multiple measurement sources in the present system. Thus, a measurement function, h, is required for each source.

As the kinematic (encoder or position sensor) measurement is of the state directly, the measurement function, $h_{NV1-k}$, is identity, with the exception of a conversion from rotation-matrix to quaternion for the end effector orientation.

Figure 6:
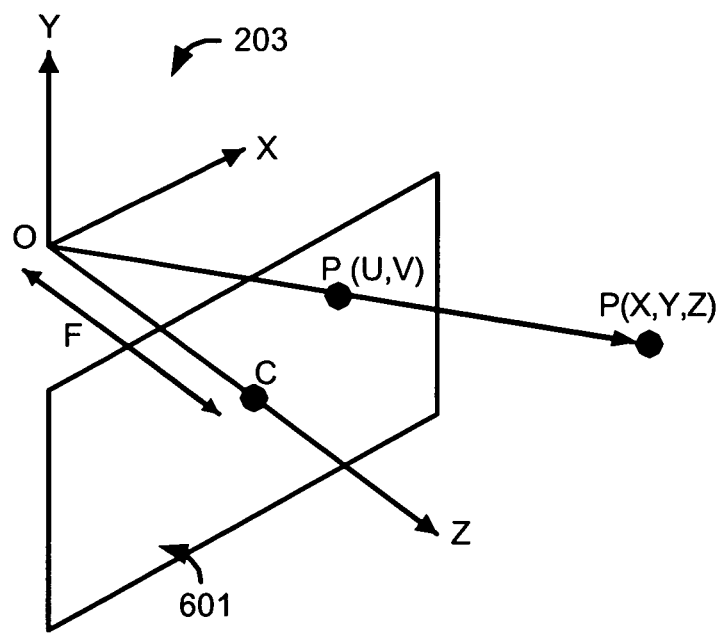
FIG. 6 illustrates a perspective projection used to relate a position in three-dimensional space to a corresponding position in two-dimensional image plane.

The second measurement, from the endoscope images, is the position (u,v) of the endoscope end-effector in the left and right image plane. The measurement function in this case is the perspective projection function, which relates a position in 3-D space to a position in image space, as shown in FIG. 6.

If a point P is assumed in the camera reference frame (of the endoscope) with coordinates (x,y,z), then its projection using a pinhole camera model is given by equation (19).

$$u_{cam} = x/z$$

$$v_{cam} = y/z \tag{19}$$

If the camera is allowed to have radial lens distortion, then the distorted u,v coordinates are given by equation (20), where $$r^2 = \left(\frac{x}{z}\right)^2 + \left(\frac{y}{z}\right)^2,$$

and $k_n$ are the radial distortion coefficients of the camera calibration.

$$u_{cam} = \frac{x}{z}(1 + k_1 r^2 + k_2 r^4 + k_3 r^6) \tag{20}$$

$$v_{cam} = \frac{y}{z}(1 + k_1 r^2 + k_2 r^4 + k_3 r^6)$$

Conversion to pixel coordinates is then performed by multiplying by the focal length, f, expressed in pixels, where c is the optical center, as given by equation (21).

$$u = f_x u_{cam} + c_x$$

$$v = f_y v_{cam} + c_y \tag{21}$$

The subscript x or y denotes the x or y component of the focal length or optical center. Note that in this discussion the contribution of tangential or skew distortion has been ignored, which would have added extra terms to the above equations.

Having defined the measurement functions, h, the partial derivatives of h with respect to the state are taken to satisfy equation (7) of the Kalman filter update cycle.

As previously described, the kinematics measurement is of the state directly. Therefore, the measurement Jacobian for the kinematics measurement is the 13×13 identity matrix, (22).

$$H_{NV1-k} = I_{13 \times 13} \tag{22}$$

Taking the partial of the vision measurement function with respect to the state, the image Jacobian is obtained, which relates end-effector translational and rotational velocities to image-space velocities.

By way of introduction, the equation for a point moving in 3-D space may be seen in equations (23).

$$\dot{u} = \frac{f_x \dot{x}}{z} - \frac{f_x x \dot{z}}{z^2} \tag{23}$$

$$\dot{v} = \frac{f_y \dot{y}}{z} - \frac{f_y y \dot{z}}{z^2}$$

When extended to a stereo vision system, where the observed point is off-axis from the center of rotation, equation set (24) is obtained. For a derivation of this equation set, see, e.g., Bijoy K. Ghosh, Ning Xi, T. J. Tarn, "Control in Robotics and Automation: Sensor Based Integration", Academic Press, San Diego, 1999.

$$H_{V1-k} = \begin{bmatrix} 0_{4 \times 7} & \begin{matrix} H_{visk1,8} & H_{visk1,9} & H_{visk1,10} & H_{visk1,11} & H_{visk1,12} & H_{visk1,13} \\ H_{visk2,8} & H_{visk1,9} & H_{visk1,10} & H_{visk1,11} & H_{visk1,12} & H_{visk1,13} \\ H_{visk2,8} & H_{visk1,9} & H_{visk1,10} & H_{visk1,11} & H_{visk1,12} & H_{visk1,13} \\ H_{visk2,8} & H_{visk1,9} & H_{visk1,10} & H_{visk1,11} & H_{visk1,12} & H_{visk1,13} \end{matrix} \end{bmatrix}_{4 \times 13} \tag{24}$$

where:

-continued $$H_{visk1,8} = f_{x1}/Z_c \qquad H_{visk2,8} = 0 \qquad (25)$$

$$H_{visk1,9} = 0 \qquad H_{visk2,9} = \frac{f_{y1}}{Z_c}$$

$$H_{visk1,10} = -\frac{f_{x1}(X_c + b/2)}{Z_c^2} \qquad H_{visk2,10} = -\frac{f_{y1}Y_c}{Z_c^2}$$

$$H_{visk1,11} = -\frac{f_{x1}(X_c + b/2)Y_t}{Z_c^2} \qquad H_{visk2,11} = -\frac{f_{y1}Z_t}{Z_c} - \frac{f_{y1}Y_cY_t}{Z_c^2}$$

$$H_{visk1,12} = \frac{f_{x1}Z_t}{Z_c} + \frac{f_{x1}(X_c + b/2)(X_t + b/2)}{Z_c^2} \qquad H_{visk2,12} = \frac{f_{y1}Y_c(X_t + b/2)}{Z_c^2}$$

$$H_{vis1,13} = -\frac{f_{x1}Y_t}{Z_c} \qquad H_{visk2,13} = \frac{f_{y1}(X_t + b/2)}{Z_c}$$

and $$H_{visk3,8} = f_{xr}/Z_c \qquad H_{visk4,8} = 0 \qquad (26)$$

$$H_{visk3,9} = 0 \qquad H_{visk4,9} = \frac{f_{yr}}{Z_c}$$

$$H_{visk3,10} = -\frac{f_{xr}(X_c + b/2)}{Z_c^2} \qquad H_{visk4,10} = -\frac{f_{yr}Y_c}{Z_c^2}$$

$$H_{visk3,11} = -\frac{f_{xr}(X_c + b/2)Y_t}{Z_c^2} \qquad H_{visk4,11} = -\frac{f_{yr}Z_t}{Z_c} - \frac{f_{yr}Y_cY_t}{Z_c^2}$$

$$H_{visk3,12} = \frac{f_{xr}Z_t}{Z_c} + \frac{f_{xr}(X_c - b/2)(X_t - b/2)}{Z_c^2} \qquad H_{visk4,12} = \frac{f_{yr}Y_c(X_t - b/2)}{Z_c^2}$$

$$H_{vis3,13} = -\frac{f_{xr}Y_t}{Z_c} \qquad H_{visk4,13} = \frac{f_{yr}(X_t - b/2)}{Z_c}$$

In the above equations (25) and (26), the variable 'b' refers to the baseline distance between the stereo cameras of the endoscope. The subscript 'l' or 'r' refers to the left or right camera, respectively. $X_c$, $Y_c$, $Z_c$ refer to the origin of the coordinate frame about which the rigid body is being rotated, and $X_t$, $Y_t$, $Z_t$ refer to the point of interest relative to the rotation origin, affixed to the rigid body, as shown in FIG. 7 wherein $X_c$, $Y_c$, $Z_c$ are the X,Y,Z coordinates of the center point $P_C$ and $X_t$, $Y_t$, $Z_t$ are the X,Y,Z coordinates of the point PT.

Figure 7:
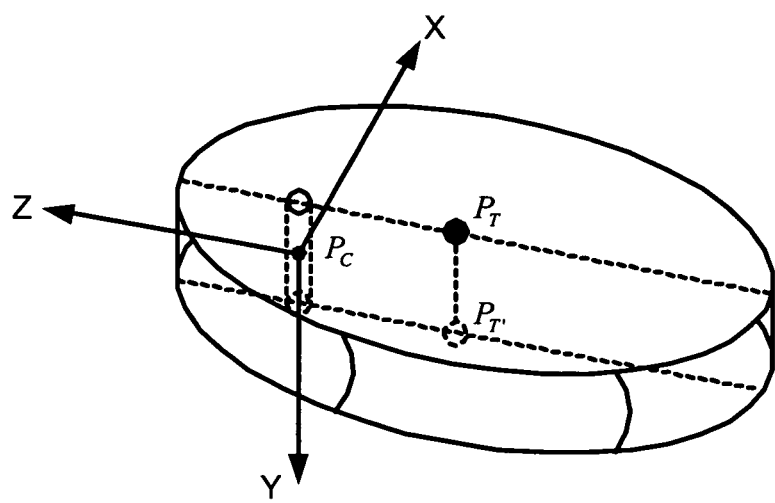
FIG. 7 illustrates a projection of a three-dimensional point on a rigid body.

Referring to FIG. 7, the point $P_C$ is the center of the pin through the tool clevis. For example, a clevis surface may be painted green, and the centroid of the resulting color blob may be tracked. The centroid of that blob would then be point $P_T$ in FIG. 7.

Based on the dot product of the end effector Y axis with the endoscope view vector, it can be determined which face of the clevis is being presented to the camera, and the sign of the distance $Y_t$ may be adjusted appropriately.

Thus, the image plane velocities can be obtained by multiplying equation (24) by the state estimate prediction, as shown as in equation (27).

$$\begin{bmatrix} \dot{u}_l \\ \dot{v}_l \\ \dot{u}_r \\ \dot{v}_r \end{bmatrix}_{4 \times 1} = H_{V1-k} \hat{X}_k^- \qquad (27)$$

To obtain the full H matrix for use in equations (3) and (5) of the Kalman filter update cycle, the two measurement Jacobians are stacked, as shown in equation (28).

$$H_k = \begin{bmatrix} H_{NV1-k} \\ H_{V1-k} \end{bmatrix}_{17 \times 13} \qquad (28)$$

As may be seen in FIG. 5, the architecture of the Kalman filter allows for several extensions, shown as dotted lines.

First, multiple endoscope video processing algorithms may be used to obtain several estimates of the tool's position in the endoscope generated image, such as shown by blocks 511-513. These may be stacked into the measurement vector, as shown in equation (18).

The endoscope vision processing algorithm, as drawn in FIG. 5, finds the tool in the image by brute force. Preferably, however, the output of the endoscope vision processing algorithm may be fed back, to reduce the search space by first looking in the area where the tool was previously found.

The state estimate output of the EKF 521 might be used, either together with the endoscope video processing output, or by itself, to reduce the search space in a similar manner. On the other hand, the endoscope video processing algorithm might simply make use of the raw kinematic input instead.

Finally, the endoscope video processing algorithm might make use of the error covariance matrix, to dynamically scale the search region based on confidence in the true tool position. This may enhance the performance of the tool tracking by bounding its search region by the error ellipse described by the error covariance matrix.

In the reverse direction, the gain matrix R may be updated if the vision processing system is able to provide a quality measure with regard to its measurement. Similarly, if the tool or an arm of its robotic mechanism has force sensors mounted on or embedded in it, then by observing the error between the actual and commanded positions, a quality measure for the kinematic information may be determined. Errors in the kinematic state measurement in this case may arise if applied forces result in deflection of the tool and/or the arm of its robotic mechanism. This quality measure may then be used to dynamically adjust gains in the EKF 521, so as to appropriately weight the kinematic state measurement's contribution to the state estimate.

Note that the EKF 521, as formulated, works in the camera reference frame 203. However, there is no requirement that this be so. In fact, it may be advantageous to use the world reference frame 201, especially if it is desired to register pre-operative or other synthetic image data with the camera image data.

Also note that in the above formulation, the stereo geometry of the stereoscopic endoscope is expressed explicitly in the $H_{V1-k}$ matrix (which is really the partial of the perspective projection operation). Alternatively, a stereo correlation may be performed between the two images, the position and orientation of the tool in 3-D extracted, and the measurement fed back into the EKF 521 directly. The result in this case should be equivalent with the new measurement function $h_{V1-k}$ being "identity".

Following is an extension to the above formulation which allows for simultaneous tool tracking and camera calibration. In the EKF formulation above, the camera parameters are assumed known or previously calibrated. The estimate of the tool end-effector position in 3-D is based upon the knowledge of these parameters through the vision measurement function, $h_{V1-k}$, as shown in the following equation:

$$z_{V1-k} = h_{V1-k}(x_k) + \text{noise} \qquad (29)$$

where $x_k$ is the state to be estimated, i.e., the 3-D position, velocity, orientation, and angular velocity of the tool, as shown in the following equation:

$$x_k = [xyz\theta_1\theta_2\theta_3\theta_4\dot{x}\dot{y}\dot{z}\omega_x\omega_y\omega_z]^T \qquad (30)$$

The vision measurement $z_{V1-k}$ is obtained by processing the left and right image planes to extract the (u,v) coordinates of the tool, as shown in the following equation:

$$z_{V1-k} = [u_l, v_l, u_r, v_r]^T \qquad (31)$$

In the previously described formulation, errors in the intrinsic camera parameters such as:

$K_1 \ldots n$: The radial distortion coefficients (left & right),
$f_x$, $f_y$: The focal length (left & right),
$c_x$, $c_y$: The camera optical center (left & right), and
$R$, $T$: The relative position/orientation of the two cameras, where R is a quaternion representation of the orientation, all contribute to the error in the tool tracking.

Calibration of these parameters can be performed by knowing the actual 3-D position of an object in the field of view, such as, for example, the tool end-effector itself. Of course, such knowledge is unfortunately not available, as it is exactly what is to be estimated.

The following method achieves simultaneous tool tracking and camera calibration based on the idea that a sequence of vision measurements, $z_{V1-k}$, will be explained in the best way, i.e. with minimum statistical error over time, by the combination of true camera parameters and true tool state.

A practical implementation of this can again be accomplished using an extended Kalman filter and expanding the state vector to include the unknown camera parameters (or a subset which needs to be estimated), $$x_{cam} = [k_{1l,r} \ldots k_{nl,r} f_{xl,r} f_{yl,r} c_{xl,r} c_{yl,r} RT]^T \qquad (32)$$

with the tool state $x_k$ from equation (29) which is now called $x_{tool_k}$:

$$x_k = [x_{tool_k} x_{cam_k}]^T \qquad (33)$$

The state transition function for the camera states is constant, i.e.:

$$x_{cam_k} = x_{cam_{k-1}} \qquad (34)$$

The vision measurement function $h_{V1-k}$ is unchanged, but its dependence on the camera parameters is made explicit so that the partial derivatives of $h_{V1-k}$ with respect to the state to be used in the Kalman filter update is:

$$H_{V1-k} = [\partial h_{V1-k}/\partial x_{tool} \partial h_{V1-k}/\partial x_{cam}] \qquad (35)$$

Using equations (32) and (34), the EKF can be computed in the same way as previously described. All the same extensions relative to continuous or discrete update options still apply. The initial value for $x_{cam}$ is to be set the best available guess and the gain matrices should weight the $x_{cam}$ states proportionally to the uncertainty in the guess.

Following is an extension to the above formulation which allows for the presence of a slowly varying systematic error in the transformation between the tool state measurement from the robot kinematics and the camera reference frame. In the EKF formulation above, the measurements from the robot position sensors and from the endoscope are assumed to be expressed in the same frame of reference or alternatively the transformation between the frame of reference of each measurement ($R_{err}$, $T_{err}$) is supposed to be known. In this latter case the measurement function $h_{NV1-k}$, as shown in the following equation $$z_{NV1-k} = h_{NV1-k}(x_k) + \text{noise} \qquad (36)$$

is easily obtained by comparison with the expression:

$$z_{NV1-k} = Ux_k + \lfloor T_x \ T_y \ T_z \ 0_{1\times 10} \rfloor \qquad (37)$$

where $$U = \begin{bmatrix} R_{err3\times 3} & 0_{3\times 4} & 0_{3\times 3} & 0_{3\times 3} \\ 0_{4\times 3} & A_{err} & 0_{4\times 3} & 0_{4\times 3} \\ 0_{3\times 3} & 0_{3\times 4} & R_{err3\times 3} & 0_{3\times 3} \\ 0_{3\times 3} & 0_{3\times 4} & 0_{3\times 3} & R_{err3\times 3} \end{bmatrix}_{13\times 13} \qquad (38)$$

with $A_{err}$ the quaternion omega matrix associated to $R_{err}$ and $T_{err} = (T_x, T_y, T_z)$.

As an initial estimate of ($R_{err}$, $T_{err}$) it is possible to compute the transformation that at one specific initialization time transforms the stereo vision measurement of the tool position into the tool position provided by the robot kinematics.

The following method achieves simultaneous tool tracking and update of ($R_{err}$, $T_{err}$) based on the idea that a sequence of endoscopic vision measurements, $z_{V1-k}$, will be explained in the best way, i.e. with minimum statistical error over time, by the combination of coherent measurements and the true tool state.

A practical implementation of this can again be accomplished using an extended Kalman filter and expanding the state vector to include the unknown parameters of the transformation ($R_{err}$, $T_{err}$) (or a subset which needs to be estimated), $$x_{err} = [R_{err} T_{err}]^T \qquad (39)$$

with $R_{err}$ the quaternion representation of the transformation rotation matrix and with the tool state $x_k$ from equation (36) which is called $x_{tool_k}$;

$$x_k = [x_{tool_k} x_{err_k}]^T \qquad (40)$$

The state transition function for the $x_{err}$ states is constant, i.e.:

$$x_{err_k} = x_{err_{k-1}} \qquad (41)$$

The measurement function $h_{NV1-k}$ is unchanged as in equation (36), but its dependence on the parameters ($R_{err}$, $T_{err}$) is made explicit so that the partial derivatives of $h_{NV1-k}$ with respect to the state to be used in the Kalman filter update is:

$$H_{NV1-k} = [\partial h_{NV1-k}/\partial x_{tool} \partial h_{NV1-k}/\partial x_{err}] \qquad (42)$$

The initial transforms for registering kinematic estimates into the camera reference frame at the current tool location as in FIG. 2 are stored in long term memory prepared offline. This transform is copied into a short term memory and is continuously updated over time according equation (40). Since this transform varies according to tool locations, the whole endoscope and tool operation space are sliced into multiple cubic cells and one transform is associated with each cubic cell. Since a tool can move to a location with different joint combinations, the transform is optimized, by taking this into account, from data collected from multiple joint combinations in the target cell.

Figure 8:
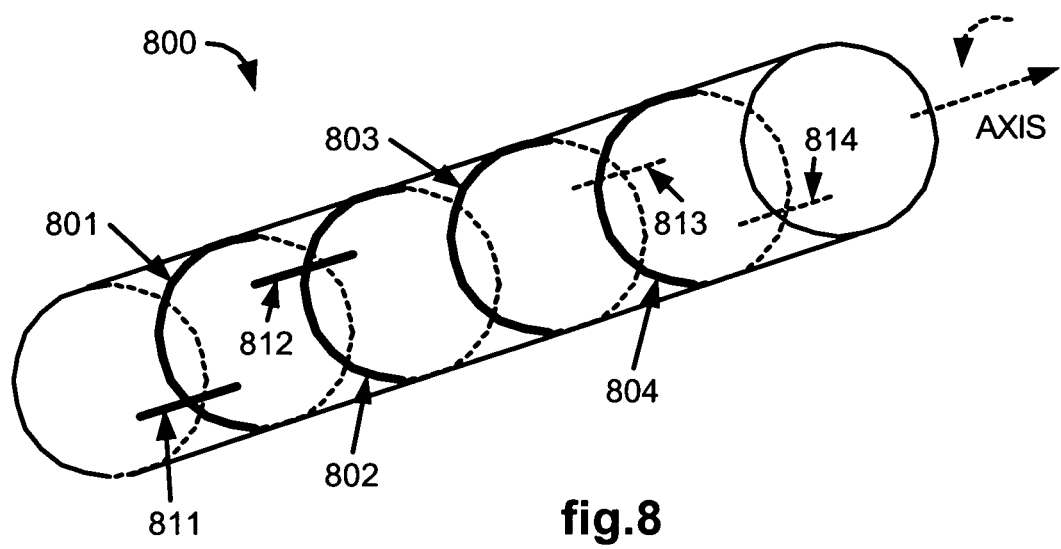
FIG. 8 illustrates a first orientation-dependent tool marker useful in performing tool tracking, utilizing aspects of the present invention.
Figure 9:
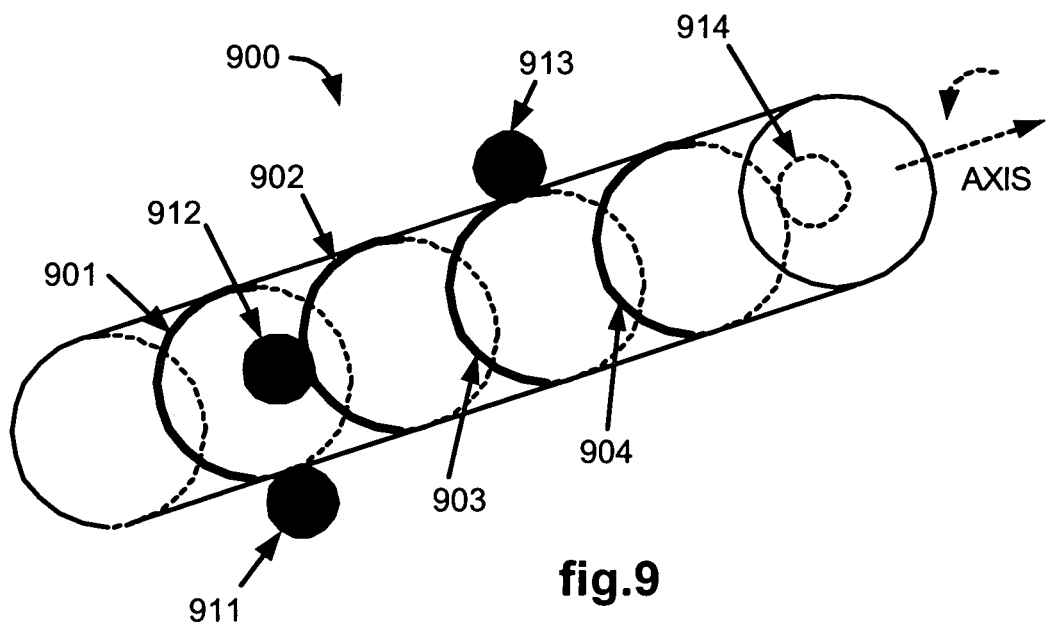
FIG. 9 illustrates a second orientation-dependent tool marker useful in performing tool tracking, utilizing aspects of the present invention.

As previously mentioned, to assist with identifying tools in a captured image, various tool identification techniques may be used, including the use of special markers. FIGS. 8 and 9 illustrate, as examples, two orientation dependent tool markers useful in performing tool tracking. The unique feature of these tool markers is that they are orientation dependent, unlike previously disclosed markers used for tracking the camera and tool(s). Therefore, if the tool has rotated along its axis, these tool markers are designed to indicate such new orientation of the tool.

Preferably, the markers are drawn or formed on the effector-end of the tool. In FIG. 8, four stripes 801-804 are drawn on the effector-end of the tool. Four line segments 811-814 are also drawn across corresponding stripes and spaced apart by 90 degrees around the axis of the tool so that as the tool rotates about the axis, the rotation may be determined by which of the line segments are in view at the time. Similarly, in FIG. 9, four stripes 901-904 are also drawn on the end of the effector-end of the tool. In this case, however, four dimples 911-914 are formed on corresponding stripes and spaced apart by 90 degrees around the axis of the tool so that as the tool rotates about the axis, the rotation may be determined by which of the dimples are in view at the time.

Figure 10:
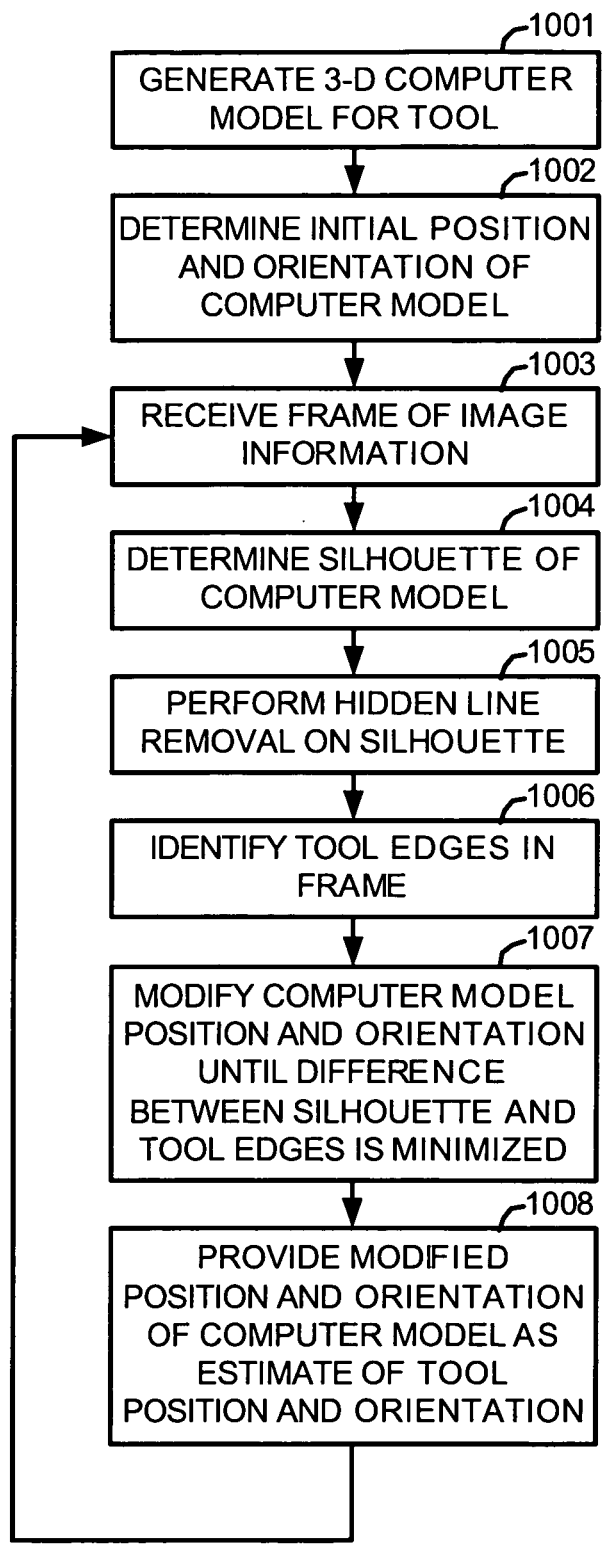
FIG. 10 illustrates a flow diagram of a computer model tool tracking method utilizing aspects of the present invention.

FIG. 10 illustrates a flow diagram of a computer model tool tracking method. An advantage of this method over other methods is that this method is generally more robust in the face of partial occlusions such as commonly encountered in surgical procedures wherein the environment is largely unstructured. For examples, in such procedures, the tools may be partially obscured by tissue, blood, or smoke; the tools may leave the field of view entirely; lighting conditions may vary greatly with time; and specular highlights may distort the normal color of the tool. The method may be used by itself for tool tracking purposes, or as one of the vision algorithms used as input to the Kalman filter described in reference to FIG. 5.

In 1001, a three-dimensional computer model of the tool is generated, for example, using well known computer-aided-design tools and techniques. In 1002, the initial position and orientation of the tool in the three-dimensional space of a surgical site is then determined by, for example, from kinematic information provided by one or more encoders coupled to a robotic mechanism used for manipulating the tool during the procedure.

In 1003, a frame of image information is received from a camera assembly viewing the surgical site. The frame in this case represents a scene or snapshot of the surgical site area taken by the camera assembly, which may include, for examples, a single camera (monoscopic) or a pair of calibrated cameras (stereoscopic).

In 1004, a silhouette of the computer model is determined in the two-dimensional view of the received frame after projecting the computer model onto the view. The silhouette in this case may be determined, for example, by a change in sign of the dot-product of the view-vector with the polygon face-normal of the edge's adjacent polygons. In 1005, the basic set of silhouette edges is then processed to remove edges which are hidden in the given tool configuration using any one of conventional hidden line removal techniques.

In 1006, edges/contours are identified or extracted from the tool image in the received frame of image information using, for example, any one of conventional edge detection techniques.

In 1007, the silhouette of the computer model is compared against the edges of the tool image in the frame, and its position and orientation modified until a difference between the modified silhouette and the detected edges of the tool image is minimized. For example, a quality metric may be defined as the sum of absolute differences between tool edge pixels extracted from the image information and their closest silhouette edges, and the position and orientation of the silhouette moved through a number of positions and orientations in the image to find a position and orientation where the quality metric is a minimum.

In 1008, the modified position and orientation of the computer model resulting from 1007 is then provided as a current estimate of the tool position and orientation, and the method effectively jumps back to 1003 to receive a next frame of image information when it is available and process it through 1003-1008 as described above using the modified position and orientation of the computer model in each case as its initial position of the computer model.

Although the various aspects of the present invention have been described with respect to a preferred embodiment, it will be understood that the invention is entitled to full protection within the full scope of the appended claims.

We claim:

1. A tool tracking and control method for minimally invasive robotic surgery, the method comprising:
   a processor determining non-endoscopically derived estimated positions of a tool by using information received from a non-endoscope device while the tool is being robotically manipulated;
   the processor determining endoscopically derived estimated positions of the tool by using information received from an endoscope while the tool is being robotically manipulated;
   the processor implementing a Bayesian filter which generates optimal estimates of the positions of the tool by processing together the non-endoscopically and endoscopically derived estimated positions of the tool; and
   the processor controlling use of one of the tool and the endoscope by using the optimal estimates of the positions of the tool.

2. The method according to claim 1, wherein the Bayesian filter is provided with an initial estimate of an average difference between a non-endoscopically derived tool position and an endoscopically derived tool position.

3. The method according to claim 2, wherein the Bayesian filter updates the estimate of the average difference between the non-endoscopically derived tool position and the endoscopically derived tool position while estimating the positions of the tool using the non-endoscopically derived tool position and the endoscopically derived tool position.

4. The method according to claim 1, wherein the non-endoscopically derived estimated position information is generated from sensor data which is received from the non-endoscope device.

5. The method according to claim 4, wherein the endoscopically derived estimated position information is generated from image data received from at least one camera of the endoscope which captures image information for an area of the body when the tool is inserted therein.

6. The method according to claim 1, wherein the Bayesian filter is a Kalman filter.

7. The method according to claim 6, wherein the Kalman filter is an extended Kalman filter.

8. The method according to claim 1, wherein the Bayesian filter is a particle filter.

9. A tool tracking and control method for minimally invasive robotic surgery, the method comprising:
 a processor generating visually derived state information of a tool from image data received from a camera viewing the tool while the tool is being robotically manipulated;
 the processor generating state vector information by combining initial values for a set of camera intrinsic parameters with the visually derived state information of the tool, wherein the camera intrinsic parameters include at least one of focal length, principal point, skew, and distortion, and wherein the state vector information is organized into a matrix that is to be multiplied by a state vector including state variables for the tool and the set of camera intrinsic parameters;
 the processor implementing a Bayesian filter and providing the state vector information to the Bayesian filter for processing according to the state vector, so the Bayesian filter generates an optimal estimate of a state of the tool and corrected values for the set of camera intrinsic parameters; and
 the processor controlling use of one of the tool and the camera by using at least one of the optimal estimate of the state of the tool and the corrected values for the set of camera intrinsic parameters.

10. The method according to claim 9, further comprising:
 the processor generating non-visually derived state information of the tool from sensor data received from one or more sensors, the sensor data including information indicative of a position of the tool; and
 the processor generating the state vector information by combining the non-visually derived state information of the tool with the initial values for the set of camera intrinsic parameters and the visually derived state information of the tool.

11. The method according to claim 10, wherein the camera is associated with an endoscope.

12. The method according to claim 10, wherein the one or more sensors are associated with a robotic mechanism used for manipulating the tool.

13. A tool tracking and control method for minimally invasive robotic surgery, the method comprising:
 a processor generating a first plurality of estimated tool positions for each point in a plurality of points in time by using at least one of sensor data associated with a robotic mechanism for manipulating the tool, sensor data associated with the tool, and image data generated by an external camera positioned so as to view an exposed end of the tool extending out of the body, while the tool is inserted through an incision in a body and being manipulated by the robotic mechanism;
 the processor generating a second plurality of estimated tool positions for each point in the plurality of points in time by using image data generated by an endoscope positioned so as to view an effector end of the tool;
 the processor determining an optimal estimated tool position for each point in the plurality of points in time by using a Bayesian technique to process the first and second pluralities of estimated tool positions; and
 the processor controlling use of one of the tool and the endoscope by using the optimal estimated tool position for each point in the plurality of points in time.

14. The method according to claim 13, wherein the robotic mechanism includes joints and linkages, wherein generating the first plurality of estimated tool positions for each point in the plurality of points in time comprises generating the first plurality of estimated tool positions by using the sensor data associated with the robotic mechanism, and wherein the sensor data associated with the robotic mechanism includes sensor data that is indicative of movement of at least one of the joints and linkages.

15. The method according to claim 13, wherein the processor generating the first plurality of estimated tool positions for each point in the plurality of points in time comprises the processor generating the first plurality of estimated tool positions by using the sensor data associated with the tool, and wherein the sensor data associated with the tool includes sensor data that is indicative of the position of the tool.

16. The method according to claim 13, wherein the Bayesian technique is a Kalman filtering technique.

17. The method according to claim 13, wherein the Bayesian technique is a particle filtering technique.

* * * * *